United States Patent
Shults et al.

(10) Patent No.: US 10,627,389 B2
(45) Date of Patent: Apr. 21, 2020

(54) METHODS OF ASSESSING CELLULAR BREAST SAMPLES AND COMPOSITIONS FOR USE IN PRACTICING THE SAME

(71) Applicant: IncellDx, Inc., Menlo Park, CA (US)

(72) Inventors: Keith Shults, Nolensville, TN (US); Amanda Noel Chargin, San Jose, CA (US); Seyedhamed Jafarianmohamady, Murfreesboro, TN (US)

(73) Assignee: IncellDx, Inc., San Carlos, CA (US)

( * ) Notice: Subject to any disclaimer, the term of this patent is extended or adjusted under 35 U.S.C. 154(b) by 808 days.

(21) Appl. No.: 15/164,778

(22) Filed: May 25, 2016

(65) Prior Publication Data

US 2016/0349232 A1 Dec. 1, 2016

Related U.S. Application Data

(60) Provisional application No. 62/166,583, filed on May 26, 2015.

(51) Int. Cl.
| | | |
|---|---|---|
| *G01N 33/483* | (2006.01) | |
| *G01N 33/574* | (2006.01) | |
| *G01N 33/50* | (2006.01) | |
| *C12Q 1/6886* | (2018.01) | |

(52) U.S. Cl.
CPC ........ *G01N 33/4833* (2013.01); *C12Q 1/6886* (2013.01); *G01N 33/5044* (2013.01); *G01N 33/5094* (2013.01); *G01N 33/57415* (2013.01); *C12Q 2600/158* (2013.01); *G01N 2333/71* (2013.01); *G01N 2333/723* (2013.01)

(58) Field of Classification Search
CPC .................................................. G01N 33/4833
USPC .......................................................... 702/19
See application file for complete search history.

(56) References Cited

U.S. PATENT DOCUMENTS

| | | | |
|---|---|---|---|
| 5,798,827 A | 8/1998 | Frank et al. | |
| 8,548,219 B2 | 10/2013 | Ortyn et al. | |
| 2009/0215053 A1 | 8/2009 | Galon et al. | |
| 2012/0122078 A1 | 5/2012 | Patterson | |
| 2012/0142089 A1 | 6/2012 | Park | |

FOREIGN PATENT DOCUMENTS

| | | |
|---|---|---|
| CN | 102713574 A | 10/2012 |
| CN | 103376228 A | 10/2013 |
| WO | WO0026666 A2 | 5/2000 |
| WO | WO2006113747 A2 | 10/2006 |
| WO | WO2007089880 A2 | 8/2007 |

OTHER PUBLICATIONS

He et al., Characteristics of mitotic cell death induced by enediyne antibiotic lidamycin in human epithelial tumor cells, International Journal of Oncology, 2002;20(2): 261-266.
Krishan et al., Detection of tumor cells in body cavity fluids by flow cytometric and immunocytochemical analysis, Diagnostic Cytopathology, 2006;34: 528-541.
Sikandar et al., Differential immune cell densities in ductal carcinoma In-Situ and invasive breast cancer: Possible role of leukocytes in early stages of carcinogenesis, Pakistan Journal of Medical Sciences, 2015;31(2):274-279.
Chargin et al., Multi-Parametric Analysis of Breast Tissue Utilizing Available Cytometric Systems, IncellDx Oncobreast 3Dx CSUPERB Poster, Department of Biology, San Francisco State University, San Francisco, CA 2IncellDx, Menlo Park, CA, Printed Aug. 24, 2016.
Pultz et al., Far beyond the usual biomarkers in breast cancer: a review, J Cancer. Jul. 4, 2014;5(7):559-71.
Ross et al., Breast cancer biomarkers and molecular medicine, Expert Rev Mol Diagn. Sep. 2003;3(5):573-85.
Saha et al., Comparative evaluation of six cytological grading systems in breast carcinoma, J Cytol. Apr.-Jun. 2013; 30(2): 87-93.
Singletary, Rating the Risk Factors for Breast Cancer, Ann Surg. Apr. 2003; 237(4): 474-482.

*Primary Examiner* — Jerry Lin
(74) *Attorney, Agent, or Firm* — Bret E. Field; Bozicevic, Field & Francis LLP

(57) ABSTRACT

Methods are provided for assessing a cellular breast sample. Aspects of the methods include flow cytometrically obtaining sample data, cellular data, and combinations thereof, and then assessing the cellular breast sample based on the obtained data. In addition, compositions, e.g., kits, systems and programming, useful in practicing various embodiments of the methods are provided.

10 Claims, 8 Drawing Sheets

METHODS OF ASSESSING CELLULAR BREAST SAMPLES AND COMPOSITIONS FOR USE IN PRACTICING THE SAME

CROSS-REFERENCE TO RELATED APPLICATIONS

Pursuant to 35 U.S.C. § 119 (e), this application claims priority to the filing date of the U.S. Provisional Patent application Ser. No. 62/166,583, filed May 26, 2015, the disclosure of which is herein incorporated by reference.

INTRODUCTION

Breast cancer is the third leading cause of cancer death in the United States. It is estimated that, in 2011, there were 2,899,726 women living with breast cancer in the United States. In 2014, it is estimated that there will be 232,670 new cases of breast cancer and an estimated 40,000 people will die of the disease in the United States. Breast cancer accounts for 22.2 deaths per 100,000 women per year and approximately 12.3% of women in the United States will be diagnosed with breast cancer at some point during their lifetime.

Cancer stage at diagnosis, which refers to the extent of a cancer in the body, determines treatment options and has a strong influence on the length of survival. Five-year relative survival rates for breast cancer diagnosed at Stage 1 (i.e., "localized", cancer is confined to the primary site) are 98.5%. However, five-year relative survival rates for breast cancer drop to 84.6% when diagnosed at Stage 2 (i.e., "regional", cancer has spread to regional lymph nodes) and to 25% when diagnosed at Stage 3 (i.e., "distant", cancer has metastasized). As such, early detection and diagnosis of breast cancer is strongly predictive of patient outcomes including treatment response and survival. As cancer metastasis is strongly correlated with advanced stage cancer determining whether a patient's cancer is or is not metastatic can be an invaluable step to a medical practitioner choosing a treatment strategy and/or making patient outcome predictions whether or not treatment is initiated (Breast cancer surveillance and epidemiology statistics retrieved from the National Cancer Institute at seer(dot)cancer(dot)gov).

One of the factors complicating diagnosis is false positive testing which leads to over diagnosis. The estimated percentage of over-diagnosis of breast cancer in the United States is 30%. Mammograms that give false-positive results are common. A 60-year-old woman screened annually for 10 years by mammography has about a 50% chance of having at least 1 false-positive that leads to follow-up testing and about a 20% chance of a false-positive that leads to biopsy (see Schwartz et al. (2000) *West J Med.* 173(5):307-312). Over diagnosis can be an outcome of testing that relies too heavily on subjective determinations, for example, such as those made by a human evaluator (e.g., a cytologist, histologist or pathologist), and or too few variables (e.g., testing of expression of a single gene or protein). It has been shown that immunohistochemistry of only Her2 protein overestimates its overexpression in 40% of all cases, which necessitates additional testing for proper diagnosis. In addition to direct consequences on a subject's medical treatment, a false-positive test result can also have indirect negative impacts on a subject's physical and psychological well-being.

In addition to diagnostic testing for medical purposes, the pharmaceutical industry relies upon determinations of cancer presence, stage, progression, and growth as measures used to evaluate treatments and new drugs. As such, owing in part those factors discussed above, the pharmaceutical industry is moving away from immunohistochemistry as a way of evaluating clinical and pre-clinical performance of new drugs and treatments and towards more quantitative methods. Furthermore, because of the vast difference in patient outcomes between primary cancers and metastatic cancers there is great interest in understanding cancer development in order to identify new therapeutic targets.

SUMMARY

Methods are provided for assessing a cellular breast sample. Aspects of the methods include flow cytometrically obtaining sample data, cellular data, and combinations thereof, and then assessing the cellular breast sample based on the obtained data. In addition, compositions, e.g., kits, systems and programming, useful in practicing various embodiments of the methods are provided.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
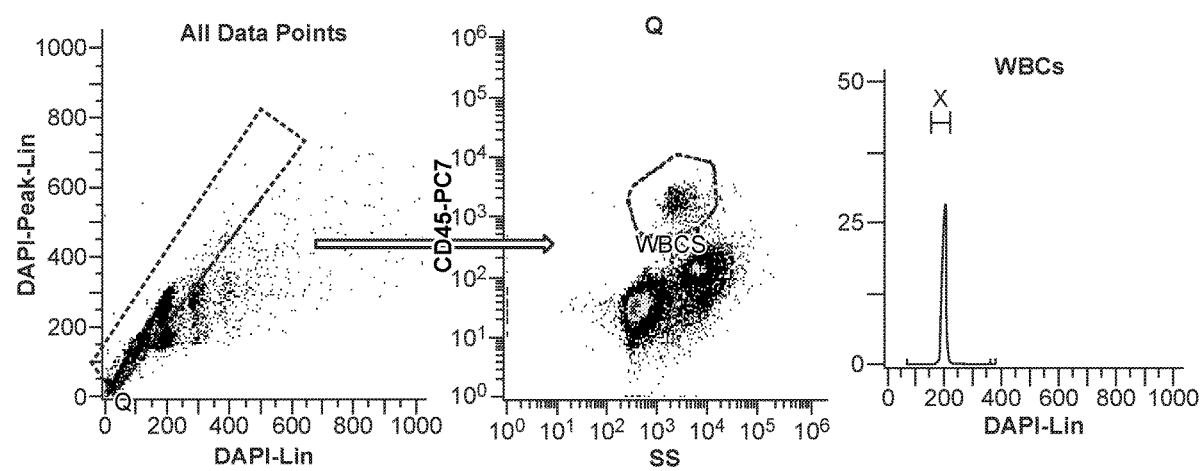
FIG. 1 depicts the gating strategy for estrogen receptor, progesterone receptor, Her2 mRNA, HER2 protein, DAPI, and CD45 labeled cells.

Methods are provided for assessing a cellular breast sample. Aspects of the methods include flow cytometrically obtaining sample data, cellular data, and combinations thereof, and then assessing the cellular breast sample based on the obtained data. In addition, compositions, e.g., kits, systems and programming, useful in practicing various embodiments of the methods are provided.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present disclosure. Nothing herein is to be construed as an admission that the present invention is not entitled to antedate such publication by virtue of prior invention. Further, the dates of publication provided may be different from the actual publication dates which may need to be independently confirmed.

Methods

As summarized above, embodiments of the invention are directed to methods of assessing a cellular breast sample, i.e., a sample of breast cells or a breast cell sample. By "cellular breast sample" is meant a sample containing cells derived, e.g., utilizing those methods as described in more detail below, from the breast of a subject, i.e., from breast tissue. According to the methods described herein, data is obtained from the sample by flow cytometrically analyzing the sample, described in more detail below, followed by evaluation of the data to make an assessment of the sample.

Data

Data obtained from a sample may include various categories of data including but not limited to, e.g., sample data and cellular data. By "sample data" is meant data pertaining to the sample as a whole and representing one or more characteristics of the sample. Sample data may be obtained through analysis of the entire sample or a portion of the sample (i.e., sampled from the sample). By "cellular data" is meant data pertaining to an individual cell of the sample and representing one or more characteristics of the particular cell. Cellular data may be expressed on a "per cell" or individual cell basis or may be expressed as a statistical characteristic (e.g., average) of 2 or more cells such as, but not limited to, all the cells of the sample or some portion of the cells of the sample, including the cells of a particular population or subpopulation.

In instances where sample data is obtained from a portion of the sample, one or more sample measurements made on the portion of the sample may be extrapolated to the entire sample as is consistent with routine sampling procedures. In some embodiments, the portion of the sample from which sample data is obtained may be up to 50% or more of the sample, including but not limited to e.g., 45% of the sample, 40% of the sample, 35% of the sample, 33% of the sample, 30% of the sample, 25% of the sample, 20% of the sample, 15% of the sample, 10% of the sample, 5% of the sample, 4% of the sample, 3% of the sample, 2% of the sample, 1% of the sample, 0.5% of the sample, 0.1% of the sample, etc., optionally including a minimum of 0.01% of the sample and a maximum of 99.99% of the sample.

In some instances, multiple portions of a sample may be analyzed in replicate so as to add confidence in extrapolation of the measured characteristic to the entire sample. The number of replicate portions of the sample analyzed will vary depending, e.g., on the particular sample characteristic being analyzed and the size of the portion of the sample. In some instances, the number of replicate measurements may be 2 or more, including but not limited to, e.g., 3 or more, 4 or more, 5 or more, 6 or more, 7 or more, 8 or more, 9 or more, 10 or more, etc., optionally including a maximum of 100 replicates. In other instances, a single measurement may be used to assess a particular sample characteristic.

Data obtained from the sample may or may not directly require the use of markers, labels, or stains to label or stain the sample in order to allow for the acquisition of the particular data characteristic. For example, in some instances, data, including sample data and cellular data, may be obtained without labeling or staining the cells of the sample. In other instances, data, including sample data and cellular data, acquisition may require labeling or staining the cells of the sample.

In certain embodiments, data obtained from the sample may include sample data obtained without requiring the detection of a label. Sample data that may be obtained without the detection of a label include but are not limited to, e.g., a count of the total number of cells in the sample (i.e., total cell count), a count of the number of single cells in the sample (i.e., single cell count), a count of the number of cells in particular volume of sample (i.e., cell count per volume or cell concentration or cell density), a count of the number of non-single cells in the sample (e.g., doublet count), a count of the number of cells of a particular size or size range in the sample (e.g., cell size count), the concentration of the number of cells of a particular size or size range in the sample (e.g., cell size concentration or cell size density), a count of the number of cells of a particular granularity or range of granularity (e.g., cell granularity count), the concentration of cells of a particular granularity or range of granularity (e.g., cell granularity concentration or cell granularity density), and the like. In some instances, the detection of such sample data without the use of a label provides certain advantages including but not limited to, e.g., the ability to use additional labels for other purposes, more rapid detection of the particular sample data characteristic, ease of use, cost-effectiveness, etc.

In certain embodiments, data obtained from the sample may include sample data obtained using the detection of a label. Sample data that may be obtained with the detection of a label includes but is not limited to those sample features described above that can be detected without a label, where such features may include but are not limited to, e.g., a count of the total number of cells in the sample (i.e., total cell count), a count of the number of single cells in the sample (i.e., single cell count), a count of the number of cells in particular volume of sample (i.e., cell count per volume or cell concentration or cell density), a count of the number of non-single cells in the sample (e.g., doublet count), a count of the number of cells of a particular size or size range in the sample (e.g., cell size count), the concentration of the number of cells of a particular size or size range in the sample (e.g., cell size concentration or cell size density), a count of the number of cells of a particular granularity or range of granularity (e.g., cell granularity count), the concentration of cells of a particular granularity or range of granularity (e.g., cell granularity concentration or cell granularity density), and the like. In some instances, the use of a label, e.g., a non-specific cell label, to detect the sample data that may be detected without a label allows for particular advantages including but not limited to, e.g., more rapid detection of the sample data, more accurate detection of the sample data, etc.

In some instances, sample data obtained using the detection of a label may include sample data that cannot be detected by flow cytometry without the use of the label including but not limited to, e.g., cell cycle data or proliferation data and the like. For example, in some instances, sample data may be obtained using a fluorescent nuclear label (e.g., a DNA label) and may include sample cell cycle data (e.g., including the count or percent of cells of the sample in one or more particular phases of the cell cycle) or sample proliferation data (e.g., including the count or percent of cells of the sample that are or are not proliferating), etc. In some instances, sample cell cycle data may include but is not limited to the count or percent of cells of the sample that are in $G_1$ phase of the cell cycle, count or percent of cells of the sample that are in $G_2$ phase of the cell cycle, count or percent of cells of the sample that are in S phase of the cell cycle, count or percent of cells of the sample that are in M phase of the cell cycle, count or percent of cells of the sample that are in $G_0$ phase of the cell cycle, and combinations thereof. Combinations of counts or percentages of cells of the sample that are in particular phases of the cell cycle include but are not limited to e.g., "post $G_1$" which includes e.g., a combination of S, $G_2$ and M.

Sample data obtained using a label also includes, where desired, negative labeling data or sample data that represents the number or percent of cells of a sample that do not label with a particular label including but not limited to, e.g., viability data obtained using a negative viability dye including but not limited to propidium iodide (PI), 7-aminoactinomycin D (7-AAD), and those available from commercial distributors such as Fixable Viability Dye eFluor 455UV/450/506/520/660/780 (Affymetrix eBioscience, San Diego, Calif.), LIVE/DEAD Fixable Blue/Violet/Aqua/Yellow stain (Life Technologies, Grand Island, N.Y.), Zombie Aqua/Green/NIR/RED/UV/Violet/Yellow (BioLegend, San Diego, Calif.) and the like.

In some instances, sample data may include combinations of sample data, including combinations of sample data obtained with and without the use of a label. For example, in some instances, sample data may include cell count or cell density data in combination with cell cycle data or cell viability data and sub-combinations thereof.

In certain embodiments, a label may be used to allow for the partitioning of cells of the sample in order to obtain data for one or more subpopulations of cells. For example, cells of the sample may be partitioned based on the presence or absence of a detected label and data may be obtained for the partitioned cells. In other instances, cells of the sample may be partitioned based on the level of a detected label (e.g., detection above a threshold level) and data may be obtained for the partitioned cells. Labels used in partitioning cells of the sample into one or more subpopulations will vary depending on the particular data to be obtained and may include but are not limited to e.g., labels of cell type markers, labels of immunophenotype markers, labels of cancer phenotype markers, non-specific cell labels and stains (e.g., fluorescent nuclear labels, DNA stains, etc.), etc. Examples of such labels and markers are described herein. In some instances, a subpopulation of cells may be cells expressing a cell type marker (e.g., detected label indicates the presence of the marker on the cells and/or the presence of the marker on the cells above a threshold level) and data is obtained based on the subpopulation of cells (e.g., the number of cells of the subpopulation in the sample, the concentration of cells of the subpopulation in the sample, etc.). For example, in some instances, data based on a cell subpopulation may include but is not limited to the number or concentration of epithelial cells in a sample, the number or concentration of white blood cells in the sample, the number or concentration of biomarker expressing cells in the sample, the number or concentration of biomarker expressing epithelial cells in the sample, the number or concentration of biomarker expressing WBCs in the sample, etc.

Any sample data parameter or cellular data parameter, including but not limited to those described herein, may be determined specifically for a partitioned subpopulation of cells. For example, in some instances, a subpopulation of cells may be partitioned based on expression of an identifying marker and one or more sample data parameters or cellular data parameters may be determined for the subpopulation. In some instances, an epithelial subpopulation of cells may be partitioned and one or more sample data parameters or cellular data parameters may be determined for the epithelial subpopulation. For example, in some instances, an epithelial subpopulation of cells may be partitioned and a cell cycle parameter may be determined for the epithelial subpopulation (e.g., the count or percentage of cells in $G_1$ phase of the cell cycle, the count or percentage of cells in S phase of the cell cycle, the count or percentage of cells in M phase of the cell cycle, the count or percentage of cells in $G_2$ phase of the cell cycle, the count or percentage of cells in post-$G_1$, etc.). In some instances, an epithelial subpopulation of cells may be partitioned and the count or percentage of epithelial cells expressing or not expressing a particular biomarker may be determined, including but not limited to e.g., where the particular biomarker is an immuno-marker (e.g., CD44, CD45, etc.).

In some instances, a marker threshold (e.g., representing a label threshold) is determined by making a comparison of the levels of marker in two separate populations of cells known to differ in their level of the subject marker. For example, a first cell population known to have a high level of Marker X is measured, e.g., on a flow cytometer, and compared to a second cell population, known to have a low level of Marker X and the comparison is used to determine a threshold level that may be used to categorize cells as either having a low or a high level of Marker X and cell populations may be partitioned accordingly.

In some instances, a marker threshold (e.g., representing a label threshold) is determined by making a comparison of the levels of marker within a population of cells, e.g., a population of cells of unknown levels of Marker X or a population of cells suspected of containing subpopulations of cells having different levels of Marker X. For example, the level of Marker X is measured on a flow cytometer of at least a sufficient number of cells such that the measurements may be plotted, e.g., on a histogram, and separation between two or more subpopulations of cells is revealed based on individual cell levels of Marker X. Accordingly, the flow cytometer operator may then determine a threshold level between the subpopulations that may be used to categorize cells as belonging to a particular subpopulation, e.g., a subpopulation having a low level of Marker X or a subpopulation having high level of Marker X and the populations may be partitioned accordingly.

In some instances, the marker threshold (e.g., representing a label threshold) is based on the limit of detection of the flow cytometer. For example, cells of a population of cells may be identified as having a particular marker (i.e., being positive for a particular marker) if the cells have any detectable level of a particular marker. Likewise, cells of a population of cells may be identified as not having a particular marker (i.e., being negative for a particular marker) if the cells do not have a detectable level of a particular marker. Accordingly, the detection level of the flow cytometer may be used to determine the marker threshold, as desired.

In some instances, the marker threshold (e.g., representing a label threshold) is based on previously determined marker levels (i.e., reference marker levels), e.g., from previously performed control experiments or previously acquired reference expression levels. For example, marker levels determined in previously analyzed samples, e.g., from cancer patients and healthy patients such as those described herein, may be used to determine marker threshold levels. In some instances, marker levels expected of cells obtained from healthy subjects may be used to determine normal marker levels such that a marker threshold that is representative of the normal marker range may be determined. In such instances, marker expression outside, i.e., above or below, the normal marker range is considered to be either above or below the particular marker threshold. In some instances, use of such previously determined marker levels or previously determined threshold levels allows analysis of cells and the identification of cellular subpopulations in the absence of a control or reference cellular sample.

Cellular data, as described herein, may be obtained for the cells of the sample as a whole or for the cells of a particular subpopulation. Cellular data may be obtained with or without the use of a label. Cellular data that may be obtained without the use of a label includes but is not limited to, e.g., cell size data, cell granularity data, cell autofluorescence data, cell volume, and the like. Cellular data obtained without the use of a label may be acquired through any convenient flow cytometric method including detection and analysis for forward scatter (FSC), side scatter (SSC), or autofluorescence (detected at any one or more fluorescence detectors), and the like.

In some instances, cellular data that includes cell volume may be collected through the use of one or more electronic detectors. For example, a measurement of cell volume may include an electronic volume measurement based on the Coulter Principle or the current impedance in an electrical field caused by the cell passing through the field (i.e., Coulter Volume). In some instances, cells of the sample prepared according to the methods described herein may maintain the electronic cell volume of unprepared cells, including unfixed cells, including at least 70% of the unfixed volume, at least 75% of the unfixed volume, at least 80% of the unfixed volume, at least 85% of the unfixed volume, at least 90% of the unfixed volume, etc., optionally including a maximum of 100% of the unfixed volume.

In some instances, cellular data may be obtained through the use of one or more cellular labels, e.g., through the binding of one or more cellular markers with a specific binding agent that binds the marker (i.e., biomarker). The specific binding agent may itself serve as a detectable label, e.g., by virtue of an inherent detectable characteristic of the specific binding member (e.g., fluorescence, magnetism, electrical charge, electrical impedance, color, reflectance, etc.) or the specific binding member may be indirectly detected through attachment or binding of a detectable label to the specific binding member. Specific binding members and detectable labels are discussed in greater detail below. Such specific binding members are useful in obtaining cellular data including but not limited to, e.g., biomarker expression, DNA content, cell cycle characteristics, cell cycle phase, cell proliferation, and the like.

In some instances, cellular data may include cellular data obtained for a population of WBCs of the sample. Cellular data for WBCs which may be evaluated in assessments as described herein will vary depending on the assay and markers used and may include any component of cellular data described as obtained for other cells and cell populations described herein, including but not limited to, e.g., cell size, cell volume, DNA content, biomarker expression, cell cycle characteristics, cell cycle phase, cell proliferation, and the like. In some instances, WBC data may include measurement of the proliferative component or the $G_1$ cell-cycle phase component of a population of WBCs. In some instances, WBC data may include measurement of the biomarker signal, or a combination of biomarker signals, of a population of WBCs. For the purposes of the methods described herein assessed biomarker signal of WBCs is not limited to immuno-markers and may include, e.g., assessment of the signal(s) of other biomarkers of other categories including but not limited to cancer and/or breast cancer biomarkers, cell adhesion biomarkers, cell cycle or cell proliferation biomarkers, and the like. In some instances, the signal of a particular biomarker or combination of biomarkers for a population of WBCs useful as data in making an assessment as described herein may be the signal of the biomarker or combination thereof above or below a particular threshold.

Biomarker data refers to any type of data from which biomarker information for the cell may be derived. In some instances, biomarker data is data that includes a signal emitted by the label of the labeled biomarker probe that is employed in the assay. The biomarker data may be in the form of the presence and amplitude of emitted light, the number of discrete positions in a cell or other object from which the light signal(s) originate(s), the relative placement of the signal sources, and the color (wavelength or waveband) of the light emitted at each position in the cell. The biomarker data may take the form of qualitative, semi-quantitative or quantitative data. Qualitative data is simply the presence or absence of the biomarker. Semi-quantitative or quantitative data is data that provides some indication of the amount, e.g., copy number, concentration, etc., of the biomarker in the cell. For example, semi-quantitative data may take the form of an indication that the copy number of a biomarker of interest is above a certain threshold number. Quantitative data provides an indication of an absolute value, e.g., copy number, amount, etc., of the biomarker in the cell. Semi-quantitative and quantitative data may be collectively referred to as biomarker quantitation data.

Aspects of the instant disclosure include combinations of data that, in combination, have greater predictive power than the individual types of data alone. Any of the data types described herein may be combined as appropriate where, as will be readily apparent to the skilled artisan, physical aspects of labeling and collecting the combined data do not significantly interfere. For example, in some instances, assessments of the cells of a sample of breast cells may include collecting combinations of sample data and cellular data and evaluating the data to make a breast cancer assessment with greater predictive power than would be obtained from the sample data or the cellular data alone. In some instances, assessments of the cells of a sample of breast cells may include collecting combinations of sample data and WBC data and evaluating the data to make a breast cancer assessment with greater predictive power than would be obtained from the sample data or the WBC data alone. In some instances, assessments of the cells of a sample of breast cells may include collecting combinations of cellular data and WBC data and evaluating the data to make a breast cancer assessment with greater predictive power than would be obtained from the cellular data or the WBC data alone. In some instances, assessments of the cells of a sample of breast cells may include collecting combinations of sample data, cellular data and WBC data and evaluating the data to make a breast cancer assessment with greater predictive power than would be obtained from the sample data, cellular data or the WBC data alone or sub-combinations thereof. In some instances, assessments of the cells of a sample of breast cells may include collecting combinations of two or more different types of sample data. In some instances, assessments of the cells of a sample of breast cells may include collecting combinations of two or more different types of cellular data. In some instances, assessments of the cells of a sample of breast cells may include collecting combinations of two or more different types of WBC data.

Samples

Samples containing breast cells may be obtained using any convenient sample collection method, including but not limited to those biopsy methods for obtaining solid tissue biopsies and biopsy aspirates. In some instances, a sample containing breast cells may be obtained as part of a separate medical procedure performed for a purpose other than obtaining the sample, including but not limited to a surgical procedure. In other instances, a sample containing breast cells may be obtained independently, e.g., not as part of a separate medical procedure. Sample collection methods will vary and will depend upon, e.g., whether the collection is or is not performed as part of an additional medical procedure, the particular type of sample to be obtained, the primary purpose for obtaining the sample and/or the method by which the sample is to be processed and/or analyzed.

In some instances, a sample may be obtained by a surgical biopsy. Any convenient and appropriate technique for surgical biopsy may be utilized for collection of a sample to be analyzed according to the methods described herein including but not limited to, e.g., excisional biopsy, incisional biopsy, wire localization biopsy, and the like. In some instances, a surgical biopsy may be obtained as a part of a surgical procedure which has a primary purpose other than obtaining the sample, e.g., including but not limited to partial mastectomy, segmental mastectomy, quadrantectomy, simple mastectomy, total mastectomy, radical mastectomy, modified radical mastectomy, skin-sparing mastectomy, breast augmentation, breast reconstruction, lymph node surgery, axillary lymph node dissection, sentinel lymph node surgery, and the like.

In some instances, a sample may be obtained by a needle biopsy. Any convenient and appropriate technique for needle biopsy may be utilized for collection of a sample to be analyzed according to the methods described herein including but not limited to, e.g., fine needle aspiration (FNA), core needle biopsy, stereotactic core biopsy, vacuum assisted biopsy, and the like.

FNA biopsy may be performed on both palpable and non-palpable lesions and involves the introduction of a small-gauge needle, e.g., ranging from 18 to 25 gauge, into the mass or suspected area and the extraction of cellular material. Whether FNA is performed with or without co-imaging may vary and will depend on various factors including whether the lesion is palpable. In instances where FNA is performed with co-imaging the technique may be referred to as image-guided FNA and may include but is not limited to radiological imaging techniques such as ultrasound, computed tomography (CT), fluoroscopy, mammography, MRI, and the like. FNA techniques, and variations thereof, useful in collecting samples as described herein will vary and selection of specific techniques will depend on various factors including but not limited to, e.g., the characteristics of the subject, the characteristics of the particular detected lesion, the analysis procedure, etc. Variations of such FNA techniques include but are not limited to, e.g., the open-ended needle (i.e., the "French technique"), the negative pressure technique, imaging-guided FNA, and the like. As such, particular FNA techniques may or may not include negative suction. For example, in the French technique FNA short, rapid strokes within the lesion cause dislodgement of cells and allow effective collection within the needle via capillary action without the need for negative suction. In some instances, e.g., when excess fluid (e.g., of a cystic lesion), a syringe with plunger removed may be employed in collecting a sample by FNA. In some instances, negative pressure may be utilized to draw the sample into a syringe. In some instances, a syringe holder or aspiration gun or aspiration handle may be used.

Core needle biopsy may be performed on both palpable and non-palpable lesions and involves the introduction of a hollow core needle into the mass or suspected area and the extraction of cellular material. Whether core needle biopsy is performed with or without co-imaging may vary and will depend on various factors including whether the lesion is palpable. In instances where core needle biopsy is performed with co-imaging the technique may be referred to as image-guided core needle biopsy or stereotactic core needle biopsy and may include but is not limited to radiological imaging techniques such as ultrasound, computed tomography (CT), fluoroscopy, mammography, MRI, and the like. Variations of such core needle biopsy techniques include but are not limited to, e.g., vacuum-assisted core biopsy, imaging-guided core biopsy, and the like. As such, particular core needle biopsy techniques may or may not include an incision made in the skin prior to insertion of the core biopsy needle. For example, in the vacuum-assisted core biopsy a small cut is made and a hollow probe is put through the cut and guided to the lesion site and then a cylinder of tissue is then pulled into the probe by vacuum pressure. In general, a core needle biopsy obtains more tissue than the described FNA technique.

In some instances, the term "needle biopsy" may generally refer any breast biopsy which can be performed without anesthesia or may require only local anesthesia and which are not considered surgical procedures. In some instances, such biopsies may utilize devices other than "needles" such as, but not limited to, those devices that may be utilized to obtain a punch biopsy, e.g., a skin punch biopsy. Such devices include but are not limited to, e.g., those devices used in the collection of skin punch biopsies commonly obtained when inflammatory breast cancer or Paget's disease is suspected.

According to the particular biopsy method employed and depending on the specifics of a particular subject and/or a subject's particular lesion one biopsy or multiple biopsies may be performed. For example, in some instances, a single biopsy, e.g., a single FNA biopsy or a single core needle biopsy, may be performed to sufficiently sample a particular subject or a particular subject's lesion. In other instances, multiple biopsies, e.g., multiple FNA biopsies or multiple core needle biopsies, may be performed for the collection of a single sample or multiple samples from a subject or a subject's lesion. In instances where multiple biopsies are collected the actual number of biopsies will vary depending on the particular subject and/or the particular lesion or lesions of the subject and, as such, may range from 2 to 10 or more biopsies, including but not limited to, e.g., 2 biopsies, 3 biopsies, 4 biopsies. 5 biopsies, 6 biopsies, 7 biopsies, 8 biopsies, 9 biopsies, 10 biopsies, etc. Multiple biopsies may be collected in a co-timely manner or may be collected over a pre-determined period of time, e.g., as part of a surveillance protocol.

A collected sample of breast cells may contain various cell types of the breast including but not limited to, e.g., cells of the lobe, cells of the lobules, cells of the ducts, mammary epithelial cells, cells of adipose tissue, adipocytes, cells of connective tissue, fibroblasts, cells of the ligaments, nerve cells, cells of the lymph vessels, cells of the lymph nodes, cells of the blood vessels, cells of the skin, cells of the nipple, cells of the areola complex, etc. A sample of breast cells may also contain cells of non-breast origin including but not limited to, e.g., cells of the blood, red blood cells, white blood cells, neutrophils, eosinophils, basophils, lymphocytes, monocytes, B cells, T cells, natural killer cells, histiocytes, and the like.

Samples of breast cells collected according to the methods described herein may be solid, semi-solid, or liquid samples. For example, in some instances, by nature of the collection technique utilized, e.g., techniques that cause the dissociation or aspiration of cells, the collected sample may be a liquid sample upon collection. In other instances, by nature of the collection technique utilized, e.g., surgical collection or core sample collection, the collected sample may be a solid or semi-solid sample upon collection. In embodiments where the collected sample is a solid or semi-solid sample the cells of the sample may dissociated to form a liquid sample following collection. Method of dissociating solid and semi-solid tissue samples include but are not limited to mechanical dissociation, chemical dissociation, enzymatic dissociation, and combinations thereof.

In some instances, the cells of the sample of breast cells may be manipulated following collection from the breast of a subject and before being processed and/or fixed for analysis as described herein. Manipulation of collected breast cells may be performed for a variety of purposes including but not limited to research purposes. For example, in some instances, collected cells may be cultured in vitro for various research purposes including but not limited to cell expansion, experimental compound or treatment testing, etc. In some instances, collected cells may be in vivo cultured or xenografted into a host animal for research purposes including but not limited to cell expansion, experimental compound or treatment testing, etc. Any convenient and appropriate in vitro cell culture and/or in vivo grafting technique may be utilized for the manipulation of cells of a sample of breast cells as described herein. Following such manipulation, e.g., in vitro or in vivo manipulation, the sample may be processed and/or the cells of the sample may be fixed and data may be collected and analyzed according to the methods described herein.

Upon collection or preparation of the sample the resultant liquid cellular sample of breast cells may be fixed and/or permeabilized as desired. As such, aspects of the methods may include fixing the cellular sample by contacting the sample with a suitable fixation reagent. Fixation reagents of interest are those that fix the cells at a desired time-point. Any convenient fixation reagent may be employed, where suitable fixation reagents include, but are not limited to: formaldehyde, paraformaldehyde, formaldehyde/acetone, methanol/acetone, IncellFP (IncellDx, Inc) etc. For example, paraformaldehyde used at a final concentration of about 1 to 2% has been found to be a good cross-linking fixative. In some instances, the cells in the sample are permeabilized by contacting the cells with a permeabilizing reagent. Permeabilizing reagents of interest are reagents that allow the labeled biomarker probes, e.g., as described in greater detail below, to access to the intracellular environment. Any convenient permeabilizing reagent may be employed, where suitable reagents include, but are not limited to: mild detergents, such as Triton X-100, NP-40, saponin, etc.; methanol, and the like.

In some instances, a collected liquid sample, e.g., as obtained from FNA that results in dissociation of the cells, is immediately contacted with solution intended to prepare the cells of the sample for further processing, e.g., fixation solution, permeabilization solution, staining solution, labeling solution, or combinations thereof, so to minimize degradation of the cells of the sample that may occur prior to preparation of the cells or prior to analysis of the cells. By "immediately contacted" is meant the cells of the sample or the sample itself is contacted with the subject agent or solution without unnecessary delay from the time the sample is collected. In some instances, a sample is immediately contacted with a preparative agent or solution in 6 or less hours from the time the sample is collected, including but not limited to, e.g., 5 hours or less, 4 hours or less, 3 hours or less, 2 hours or less, 1 hours or less, 30 min. or less, 20 min. or less, 15 min. or less, 10 min. or less, 5 min. or less, 4 min. or less, 3 min. or less, 2 min. or less, 1 min. or less, etc., optionally including a lower limit of the minimum amount of time necessary to physically contact the sample with the preparative agent or solution, which may, in some instances be on the order of 1 sec. to 30 sec or more.

Aspects of embodiments of the methods include preparation of the sample and/or fixation of the cells of the sample performed in such a manner that the prepared cells of the sample maintain characteristics of the unprepared cells, including characteristics of unprepared cells in situ, i.e., prior to collection, and/or unfixed cells following collection but prior to fixation and/or permeabilization and/or labeling. Such characteristics that may be maintained include but are not limited to, e.g., cell morphological characteristics including but not limited to, e.g., cell size, cell volume, cell shape, etc. The preservation of cellular characteristics through sample preparation may be evaluated by any convenient means including, e.g., the comparison of prepared to cells to one or more control samples of cells such as unprepared or unfixed or unlabeled samples. Comparison of cells of a prepared sample to cells of an unprepared sample of a particular measured characteristic may provide a percent preservation of the characteristic that will vary depending on the particular characteristic evaluated. The percent preservation of cellular characteristics of cells prepared according to the methods described herein will vary and may range from 50% maintenance or more including but not limited to, e.g., 60% maintenance or more, 65% maintenance or more, 70% maintenance or more, 75% maintenance or more, 80% maintenance or more, 85% maintenance or more, 90% maintenance or more, etc., and optionally with a maximum of 100% maintenance. In some instances, preservation of a particular cellular characteristic may be evaluated based on comparison to a reference value of the characteristic (e.g., from a predetermined measurement of one or more control cells, from a known reference standard based on unprepared cells, etc.).

As described herein, in certain embodiments, the cells of the sample may be labeled. Cellular labeling may be achieved through the use of one or more labeling reaction mixtures. In preparing the reaction mixture, the sample may be contacted or combined with one or more specific binding agents (e.g., labeled biomarker probes) using any convenient protocol. Contacting and/or combining may be carried out with mixing, as desired. Contact of the sample with the one or more specific binding agent is performed under incubation conditions that provide for binding of the agents to their respective biomarkers, if present, on or in the cells of the sample. In some instances, the agent and samples are contacted and combined at a temperature ranging from 15° C. to 50° C., such as from 20° C. to about 45° C. Contact may be performed with mixing or agitation, e.g., with vortexing etc., to provide for sufficient combination of the reaction components and the sample.

The resultant reaction mixture may then be maintained or incubated for a period of time prior to obtaining data on a flow cytometer (e.g., sample data and/or cellular data as described in greater detail below). In some instances, the reaction mixture is incubated at a temperature ranging from 15° C. to 50° C., such as from 20° C. to about 45° C. for a period of time ranging from about 30 minutes to 72 hours, such as 1 hour to 24 hours, including 1 hour 15 to 3 hours. Following the above incubation step, the sample may be assayed immediately or stored for assay at a later time. If stored, in some embodiments the sample is stored at a reduced temperature; e.g., on ice.

Where desired, the resultant reaction mixture and labeled cells of the sample may be washed, e.g., to remove any unbound agents and other sample components. Washing may be performed using any convenient protocol, e.g., by combining the reaction mixture with a suitable wash buffer and separating the cells from the fluid. A given washing protocol may include one or more distinct washing steps, as desired. Following any washing protocol, the labeled cells may be re-suspended in a suitable liquid, e.g., the washing buffer or another buffer (e.g., running buffer), for subsequent analysis, e.g., via flow cytometric analysis.

Following preparation of the sample and/or fixation of the cells of the sample, the sample may be processed to obtain data immediately or data may not be obtained from the sample for a period of time, e.g., allowing storage and/or transport of the sample. The length of the period of time before a sample is processed without detrimental effects on data collection will depend on various factors including but not limited to, e.g., the overall stability of the sample, the sample storage conditions, whether labeling was used in preparing the sample and if so what particular labels were used in labeling the cells of the sample, and/or the particular sample preparation, including cell fixation conditions, of the sample. By "without detrimental effects on data collection" is meant that there is no significant negative effect on any aspect of data collected from the sample, including, e.g., sample data and/or cellular data, such that data obtained and/or an assessment made from the sample following a period of time after preparation is essentially equal to the data or the assessment that would be obtained immediately after preparation. For example, in some instances the use of stable cell fixatives preserves the cells and cellular labeling of a sample such that the sample may be processed for data collection many days following sample collection and preparation and the data obtained is sufficient to evaluate the cells and/or make an assessment. Labeled samples that may be processed following a period of time include but are not limited to, e.g., antibody labeled samples, stained (e.g., DNA stained) samples, mRNA labeled samples, and the like. The time period during which there are no detrimental effects on data collection will vary depending on various factors discussed above and may range from 8 hours to 10 days or more including but not limited to, e.g., 12 or more hours, 1 day or more, 2 days or more, 3 days or more, 4 days or more, 5 days or more, 6 days or more, 7 days or more, 8 days or more, etc.

Agents and Labels

A variety of different types of specific binding agents may be employed, where the particular type of binding agent is selected based, at least in part, on the particular type of molecule of the marker of interest. Specific binding agents of interest include antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'$_2$ fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. Nucleic acid binding agents of interest are nucleic acids that specifically bind or specifically hybridize to biomarker nucleic acids in a cell. The length of these nucleic acids may vary, so long as it is sufficient for the oligonucleotide to serve as a specific binding agent, and in some instances ranges from 13 to 100 nt, such as 14 to 50 nt, e.g., 15 to 25 nt, including but not limited to, e.g., 15 nt, 16 nt, 17 nt, 18 nt, 19 nt, 20 nt, 21 nt, 22 nt, 23 nt, 24 nt, and 25 nt. The oligonucleotides that make up these nucleic acid binding agents may be DNA or RNA, or a synthetic analogue thereof, as desired.

As described above, a specific binding agent may itself serve as a detectable label or may include an attached detectable label or may be bound by a detectable label thus allowing detection. Therefore, in addition to a specific binding domain that specifically binds or specifically hybridizes to the biomarker of interest, the specific binding agent may further include or may be bound by or attached to a detectable label. Of interest as detectable labels are fluorescent dyes. Fluorescent dyes (fluorophores) can be selected from any of the many dyes suitable for use in imaging applications (e.g., fluorescent microscopy) and flow cytometry applications. A large number of dyes are commercially available from a variety of sources, such as, for example, Molecular Probes (Eugene, Oreg.) and Exciton (Dayton, Ohio). Examples of fluorophores of interest include, but are not limited to, 4-acetamido-4'-isothiocyanatostilbene-2, 2'disulfonic acid; acridine and derivatives such as acridine, acridine orange, acridine yellow, acridine red, and acridine isothiocyanate; 5-(2'-aminoethyl)aminonaphthalene-1-sulfonic acid (EDANS); 4-amino-N-[3-vinylsulfonyl)phenyl] naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumarin 151); cyanine and derivatives such as cyanosine, Cy3. Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo) benzoic acid (DABCYL); 4-dimethylaminophenylazophenyl-4'-isothiocyanate (DABITC); eosin and derivatives such as eosin and eosin isothiocyanate: erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, Oreg.) and Exciton (Dayton, Ohio).

Also of interest as specific binding members are those nucleic acid dyes or stains containing intrinsic fluorescence including those that specifically label DNA. Dyes and stains that are specific for DNA (or preferentially bind double stranded polynucleotides in contrast to single-stranded polynucleotides) and therefore may be employed as non-specific stains include, but are not limited to: Hoechst 33342 (2'-(4-Ethoxyphenyl)-5-(4-methyl-1-piperazinyl)-1H,1'H-2,5'-bibenzimidazole trihydrochloride) and Hoechst 33258 (4-[6-(4-Methyl-1-piperazinyl)-1',3'-dihydro-1H,2'H-2,5'-bibenzimidazol-2'-ylidene]-2,5-cyclohexadien-1-one trihydrochloride) and others of the Hoechst series; SYTO 40, SYTO 11, 12, 13, 14, 15, 16, 20, 21, 22, 23, 24, 25 (green); SYTO 17, 59 (red), DAPI, DRAQ5™ (an anthraquinone dye with high affinity for double stranded DNA), YOYO-1, propidium iodide, YO-PRO-3, TO-PRO-3. YOYO-3 and TOTO-3, SYTOX Green, SYTOX, methyl green, acridine homodimer, 7-aminoactinomycin D, 9-amino-6-chloro-2-methoxyactridine. Depending on the particular stain and assay, the stain may serve in detection of DNA, detection of nuclei, quantitation of DNA, quantitation of nuclei, cell cycle indicator, cell proliferation indicator, DNA integrity indicator, etc.

Where multiple distinct labeled biomarker probes are employed, the label of each distinct probe may be chosen to provide a distinguishable signal. For example, in embodiments where first and second distinct labeled biomarker probes are employed, the label in the second probe is a fluorescent label which produces a fluorescent signal that is distinguishable from the first fluorescent signal of the label of the first probe. Accordingly, the first and second fluorescent signals produced upon excitation of the first and second fluorescent labels are distinguishable from each other, meaning that both can be detected at the same time and that the signal from one does not modify or change the signal from the other. Each distinct label may produce signals that are distinguishable from any other label. For example, the cells may be stained with a third fluorescent label which produces a third fluorescent signal that is distinguishable from the first and second fluorescent signals.

Specific binding agents that find use in detection and/or measurement of biomarkers as described herein include but are not limited to specific binding agents that bind immuno-markers, specific binding agents that bind cancer and/or breast cancer biomarkers, specific binding agents that bind cell adhesion biomarkers, specific binding agents that bind cell cycle or cell proliferation biomarkers, and the like.

Immuno-markers, as used herein, refer to those cellular markers (e.g., cell surface markers and intracellular markers) that bind components of immune cells. Immuno-markers include but are not limited to those cell surface molecules identified as cluster of differentiation (CD) antigens which historically provided targets for immunophenotyping. CD antigens and immuno-markers in general may be expressed by one or more different immune cell types. However, CD antigens and immuno-markers generally are not exclusively expressed on immune cell types and in many cases immuno-markers may also be expressed on non-immune cell types including but not limited to e.g., epithelial cells. Immuno-markers useful in the methods described herein will vary depending on the particular assay and/or the particular cell type and/or cell population to be detected. In some instances, immuno-markers that find use in the methods described herein include but are not limited to, e.g., CD44, CD45, and the like.

Breast cancer biomarkers as used herein, refer to those cellular markers (e.g., cell surface markers and intracellular markers) that bind gene products (e.g., mRNA, protein, etc.) that are associated with cancer and/or cancer progression and those specifically associated with breast cancer and breast cancer progression (e.g., including progression to breast cancer metastasis). In some instances, cancer biomarkers and breast cancer biomarkers that find use in the methods described herein may include but are not limited to, e.g., estrogen receptor protein, estrogen receptor transcript, progesterone receptor protein, progesterone receptor transcript, human epidermal growth factor receptor 2 (HER2) protein, HER2 transcript, phosphorylated Histone H2A.X (p-H2A.X), cleaved Caspase 3, and the like. In other instances, assessment of cells of a sample may include detection and/or measurement of breast cancer biomarkers including but not limited to, e.g., serine protease urokinase-type plasminogen activator (uPA), uPA inhibitor (PAI-1). Thomsen-Friedenreich (TF) antigen, mammaglobin (h-MAM), osteopontin, fibroblast growth factor receptor (FGFR) family members (including, e.g., FGFR2), phosphatase and tensin homolog (PTEN), Sirtuins (SIRT) family members, zinc finger protein Snail1, twist-related protein 1 (TWIST1), zinc finger E-box-binding homeobox 1 (ZEB1), estrogen receptor alpha, estrogen receptor beta, p53, Receptor tyrosine-protein kinase erbB-2, and the like.

Cell adhesion biomarkers as used herein, refer to those cellular markers (e.g., cell surface markers and intracellular markers) that bind to components of the cell involved in cell adhesion, e.g., cell-to-cell adhesion, cell-to-ECM (extra cellular matrix) adhesion, etc. Such cell adhesion components may or may not have additional cell signaling roles and may be associated with epithelial-to-mesenchymal transition related to metastasis and/or cancer progression. Cell adhesion biomarkers useful in the methods described herein will vary depending on the particular assay and/or the particular cell type and/or cell population to be detected. In some instances, cell adhesion biomarkers that may find use in the methods described herein include but are not limited to, e.g., vimentin protein, vimentin transcript, E-cadherin protein, E-cadherin transcript, metadherin (MTDH, LYRIC, AEG-1, etc.) protein, MTDH transcript, and the like.

Cell cycle biomarkers, as used herein, refer to those cellular markers (e.g., cell surface markers and intracellular markers) that bind components of the cell cycle machinery of the cell. Cell cycle biomarkers may be useful, in some instances, in collecting cellular data related to cell cycle phase or whether or not a cell is proliferative. Cell cycle biomarkers useful in the methods described herein will vary depending on the particular assay and/or the particular cell type and/or cell population to be detected. In some instances, cell cycle biomarkers that may find use in the methods described herein include but are not limited to, e.g., Ki67, cyclin D1, cyclin E, and the like.

The above-described markers include intracellular markers. As used herein, the term "intracellular markers" refers to components of the cell that are within the cell beyond the outer surface of the plasma membrane. Such components may be or may be within any interior component of the cell including but not limited to the inner surface of the plasma membrane, the cytoplasm, the nucleus, mitochondria, endoplasmic reticulum, etc. As such, labeling or detection of intracellular markers requires transport of a specific label or specific binding agent of the intracellular marker across at least the outer surface of the plasma membrane. In some instances, a label or specific binding agent for an intracellular marker may be membrane permeable thus not requiring modulation of membrane permeability for labeling of the intracellular marker. In some embodiments, a label or specific binding agent for an intracellular marker may be membrane impermeable thus requiring modulation of membrane permeability for labeling of the intracellular marker, including, e.g., preparation and or treatment of the cells with one or more permeabilizing reagents as described herein.

The above-described markers include cell surface markers. As used herein, the term "cell surface markers" refers to components of the cell that are at least exposed, partially or completely, on the outer surface of the plasma membrane of cell and thus may be accessed without modulating cell permeability, e.g., without the use of one or more permeabilizing reagents as described herein. In some instances, cell surface markers include components of the cell that have a portion exposed on the outer surface of the cell membrane but also contain an intracellular portion and/or a transmembrane portion.

As described herein and as will be readily apparent to one or ordinary skill in the art, any combination of the agents and labels described herein may be employed in the cell assessment methods described provided the combination is appropriate and the components do not physically or optically interfere. For example, where alterations or substitutions of particular labels can and/or should be employed in order to allow for the combination of two or more desired components is within the skill of the ordinary artisan. As a non-limiting example, where a particular fluorescent label of a biomarker interferes optically (e.g., has an overlapping emission spectra) with a desired DNA labeling agent of a particular emission wavelength, the fluorescent label of the biomarker may be substituted with a different fluorescent label having no or less emission spectra overlap with the desired DNA labeling agent.

Flow Cytometry

As summarized above, methods of the invention include flow cytometrically analyzing a sample to obtain data. Flow cytometry is a methodology using multi-parameter data for identifying and distinguishing between different particle (e.g., cell) types i.e., particles that vary from one another in terms of label (wavelength, intensity), size, etc., in a fluid medium. In flow cytometrically analyzing the sample prepared as described above, an aliquot of the sample is first introduced into the flow path of the flow cytometer. When in the flow path, the cells in the sample are passed substantially one at a time through one or more sensing regions, where each of the cells is exposed separately and individually to a source of light at a single wavelength (or in some instances two or more distinct sources of light) and measurements of cellular parameters, e.g., light scatter parameters, and/or biomarker parameters, e.g., fluorescent emissions, as desired, are separately recorded for each cell. The data recorded for each cell is analyzed in real time or stored in a data storage and analysis means, such as a computer, for later analysis, as desired.

More specifically, in a flow cytometer, the cells are passed, in suspension, substantially one at a time in a flow path through one or more sensing regions where in each region each cell is illuminated by an energy source. The energy source may include an illuminator that emits light of a single wavelength, such as that provided by a laser (e.g., He/Ne or argon) or a mercury arc lamp with appropriate filters. For example, light at 488 nm may be used as a wavelength of emission in a flow cytometer having a single sensing region. For flow cytometers that emit light at two distinct wavelengths, additional wavelengths of emission light may be employed, where specific wavelengths of interest include, but are not limited to: 405 nm, 535 nm, 561 nm, 635 nm, 642 nm, and the like.

In series with a sensing region, detectors, e.g., light collectors, such as photomultiplier tubes (or "PMT"), an avalanche photodiode (APD), etc., are used to record light that passes through each cell (generally referred to as forward light scatter), light that is reflected orthogonal to the direction of the flow of the cells through the sensing region (generally referred to as orthogonal or side light scatter) and fluorescent light emitted from the cells, if it is labeled with fluorescent marker(s), as the cells passes through the sensing region and is illuminated by the energy source. Each type of data that is obtained, e.g., forward light scatter (or FSC), orthogonal light scatter (SSC), and fluorescence emissions (FL1, FL2, etc.), comprise a separate parameter for each cell (or each "event").

Flow cytometers may further include one or more electrical detectors. In certain embodiments, an electrical detector may be employed for detecting a disturbance caused by a particle or cell passing through an electrical field propagated across an aperture in the path of the particles/cells. Such flow cytometers having electrical detectors will contain a corresponding electrical energy emitting source that propagates an electrical field across the flow path or an aperture through which cells are directed. Any convenient electrical field and/or combination of fields with appropriate detector(s) may be used for the detection and/or measurement of particles (or cells) passing through the field including but not limited to, e.g., a direct current electrical field, alternating current electrical field, a radio-frequency field, and the like.

Flow cytometers further include data acquisition, analysis and recording means, such as a computer, wherein multiple data channels record data from each detector for each cell as it passes through the sensing region. The purpose of the analysis system is to classify and count cells wherein each cell presents itself as a set of digitized parameter values and to accumulate data for the sample as a whole. In flow cytometrically assaying cells in methods of the instant disclosure, the flow cytometer may be set to trigger on a selected parameter in order to distinguish the cells of interest from background, noise and/or a preset limit. "Trigger" refers to a preset threshold for detection of a parameter. It is typically used as a means for detecting passage of cell through the laser beam or electrical field. Detection of an event which exceeds the threshold for the selected parameter triggers acquisition of data for the cells, including light scatter and fluorescence data. Data is not acquired for cells or other components in the medium being assayed which cause a response below the threshold. In some instances, the trigger parameter may be the detection of forward scattered light caused by passage of a cell through the light beam. The flow cytometer then detects and collects data for the cell, including light scatter data, fluorescence data, and the like.

A particular subpopulation of interest is then further analyzed by "gating" based on the data collected for the entire population. To select an appropriate gate, the data is plotted so as to obtain appropriate separation of subpopulations, e.g., by adjusting the configuration of the instrument, including e.g., excitation parameters, collection parameters, compensation parameters, etc. In some instances, this procedure is done by plotting forward light scatter (FSC) vs. side (i.e., orthogonal) light scatter (SSC) on a two dimensional dot plot. The flow cytometer operator then selects the desired subpopulation of cells (i.e., those cells within the gate) and excludes cells which are not within the gate. Where desired, the operator may select the gate by drawing a line around the desired subpopulation using a cursor on a computer screen. Only those cells within the gate are then further analyzed by plotting the other parameters for these cells, such as fluorescence.

Any flow cytometer that is capable of obtaining both the sample data and cellular data, e.g., as described above, from the same aliquot of a liquid sample may be employed. Non-limiting examples of flow cytometer systems of interest are those available from commercial suppliers including but not limited to, e.g., Becton-Dickenson (Franklin Lakes, N.J.), Life Technologies (Grand Island, N.Y.), Acea Biosciences (San Diego, Calif.), Beckman-Coulter, Inc. (Indianapolis, Ind.), Bio-Rad Laboratories, Inc. (Hercules, Calif.), Cytonome, Inc. (Boston, Mass.). Amnis Corporation (Seattle, Wash.), EMD Millipore (Billerica, Mass.), Sony Biotechnology, Inc. (San Jose, Calif.), Stratedigm Corporation (San Jose, Calif.), Union Biometrica, Inc. (Holliston, Mass.), Cytek Development (Fremont, Calif.), Propel Labs, Inc. (Fort Collins, Colo.), Orflow Technologies (Ketchum, Id.), handyem inc. (Québec, Canada), Sysmex Corporation (Kobe, Japan), Partec Japan, Inc. (Tsuchiura, Japan), Bay bioscience (Kobe, Japan), Furukawa Electric Co. Ltd. (Tokyo, Japan), On-chip Biotechnologies Co., Ltd (Tokyo, Japan), Apogee Flow Systems Ltd. (Hertfordshire, United Kingdom), and the like.

In some instances, methods as described herein may be performed using a flow cytometer system having a single detector designated for detection and data acquisition of each data component, e.g., cellular data component or sample data component, used in evaluating the sample, detection of a particular cell type, and/or making an assessment of the sample. For example, in some instances, a method utilizing two fluorescent labels may be performed using a flow cytometer system having a single detector designated for detection of the first fluorescent label and a second detector designated for detection of the second label.

In some instances, methods as described herein may be performed using a flow cytometer system having a single detector designated for detection and data acquisition of multiple data components, e.g., cellular data component(s) or sample data component(s) or combinations of components thereof, used in evaluating the sample, detection of a particular cell type, and/or making an assessment of the sample. In some instances, such detectors configured for acquisition of multiple (i.e., two or more) data components may be utilized in sequential data acquisition, meaning that the multiple data components are acquired one at a time in sequence. In some instances, such detectors configured for acquisition of multiple data components may be utilized in simultaneous data acquisition, meaning that the multiple data components are acquired at one time simultaneously and the individual data components are later separated or parsed (e.g., optically within the detector, electrically within the detector, electronically within a signal processing module). In some instances, a detector may utilize both sequential data acquisition and simultaneous data acquisition depending on the configuration of the flow cytometry system and the desired analysis to be performed. Flow cytometry system are not limited to designated detectors and multi-detectors and may include both detectors that are designated for detection of a single data component and detectors that detect multiple data components.

Flow cytometric system configurations, components and variations thereon are further described below.

Sample Evaluation

Aspects of the methods of the subject disclosure include evaluating a cellular breast sample, e.g., in the form of a liquid sample of breast cells, by obtaining data on a flow cytometer. As described herein, different data components, e.g., sample data and cellular data, may be combined in such an evaluation. In some instances, the evaluation has better predictive power (i.e., can support a conclusion more strongly) than any of the individual data components when used alone.

Evaluations may be performed by any convenient or appropriate means depending on the data obtained, the type of cellular sample, and/or the purpose for making the evaluation. For example, in some instances an evaluation of a sample is made by considering the combined data obtained from the sample. In some instances, an evaluation includes comparison of the combined data to one or more controls or reference values. In other instances, an evaluation is made by implementation of an algorithm or decision tree that references the obtained data. In other instances, an evaluation is made by implementation of statistical testing that references the obtained data, including, e.g., testing of a statistical model. Depending on the particular data obtained and/or the purposes of making the evaluation, an algorithm, decision tree may, or statistical test may be implemented by a computer, e.g., utilizing the processing function of the computer to perform mathematical steps that could not be reliably performed by a person.

In some instances, methods described herein may include the detection of a particular cell type in the sample and/or identification of a particular cell type in the sample. For example, in some instances, the methods include determining that the assayed cellular sample includes cancerous cells (i.e., that cancerous cells are detected in the sample). In these embodiments, the methods include identifying the presence of one or more cancerous cells in the sample, where the identification is made based on the obtained data, e.g., sample data and/or cellular data as described above.

In some instances, the methods include determining that the assayed cellular sample includes non-cancerous cells, where the presence of the non-cancerous cells is indicative of cancer in the subject. In these embodiments, the methods include identifying the presence of (i.e., detecting) one or more non-cancerous cells in the sample, where the identification is made based on the obtained data, e.g., sample data and/or cellular data as described above. In certain instances, such non-cancerous cells that are indicative of cancer in the subject include WBCs and/or one or more particular subpopulations of WBCs.

In some instances, the methods include determining that the assayed cellular sample includes certain cancerous cells and/or certain non-cancerous cells, where the presence of the certain cancerous cells and/or certain non-cancerous cells is indicative of metastatic cancer in the subject. In these embodiments, the methods include identifying the presence of (i.e., detecting) one or more cancerous cells and/or one or more non-cancerous cells in the sample, where the identification is made based on the obtained data, e.g., sample data and/or cellular data as described above.

In some instances, evaluations of obtained sample data may be based on pre-determined sample data parameters. Pre-determined sample data parameters may be reference values (e.g., reference values provided for comparison to obtained experimental values) or pre-determined sample data may be user-defined (e.g., through measuring a sample data parameter of a control sample (e.g., a healthy control, a cancerous control, or other reference control and combinations thereof). Pre-determined sample data parameters may be provided or user-defined for any sample data, e.g., including those described herein.

In some instances, pre-determined sample data parameters may include sample cell density parameters. For example, in some instances, obtained sample data may be evaluated in comparison to a pre-determined sample cell density of a known healthy sample ranging from less than 10,000 to 30,000 cells per volume of analyzed sample, e.g., 300 µl of analyzed sample, or more including but not limited to, e.g., 10,000 cells per 300 µl of analyzed sample, 15,000 cells per 300 µl of analyzed sample, 20,000 cells per 300 µl of analyzed sample, 25,000 cells per 300 µl of analyzed sample, 30,000 cells per 300 µl of analyzed sample, etc. In some instances, the pre-determined sample cell density data parameter may be a sample cell density threshold indicative of a healthy sample where a sample cell density at or below the threshold indicates a likelihood that the sample is a healthy sample. For example, a sample cell density threshold indicative of a healthy sample may include but is not limited to a sample cell density of 80,000 or less cells per volume of analyzed sample, e.g., 300 µl of analyzed sample, including but not limited to, e.g., 80,000 or less cells per 300 µl of analyzed sample, 70,000 or less cells per 300 µl of analyzed sample, 60,000 or less cells per 300 µl of analyzed sample, 50,000 or less cells per 300 µl of analyzed sample, 40,000 or less cells per 300 µl of analyzed sample, 30,000 or less cells per 300 µl of analyzed sample, 20,000 or less cells per 300 µl of analyzed sample, etc.

In some instances, obtained sample data may be evaluated in comparison to a pre-determined sample cell density of a known tumor sample ranging from less than 80,000 to 1,000,000 cells per volume of analyzed sample, e.g., 300 µl of analyzed sample, or more including but not limited to, e.g., 80,000 cells per 300 µl of analyzed sample, 90,000 cells per 300 µl of analyzed sample, 100,000 cells per 300 µl of analyzed sample, 110,000 cells per 300 µl of analyzed sample, 120,000 cells per 300 µl of analyzed sample, 130,000 cells per 300 µl of analyzed sample, 140,000 cells per 300 µl of analyzed sample, 150,000 cells per 300 µl of analyzed sample, 160,000 cells per 300 µl of analyzed sample, 170,000 cells per 300 µl of analyzed sample, 180,000 cells per 300 µl of analyzed sample, 190,000 cells per 300 µl of analyzed sample, 200,000 cells per 300 µl of analyzed sample, etc. In some instances, the pre-determined sample cell density data parameter may be a sample cell density threshold indicative of a tumor sample where a sample cell density at or above the threshold indicates a likelihood that the sample is a tumor sample. For example, a sample cell density threshold indicative of a tumor sample may include but is not limited to a sample cell density of 50,000 or more cells per volume of analyzed sample, e.g., 300 µl of analyzed sample, including but not limited to, e.g., 50,000 or more cells per 300 µl of analyzed sample, 60,000 or more cells per 300 µl of analyzed sample, 70,000 or more cells per 300 µl of analyzed sample, 80,000 or more cells per 300 µl of analyzed sample, 90,000 or more cells per 300 µl of analyzed sample, 95,000 or more cells per 300 µl of analyzed sample, 100,000 or more cells per 300 µl of analyzed sample, 105,000 or more cells per 300 µl of analyzed sample, etc.

In some instances, obtained sample data may be evaluated in comparison to a pre-determined sample cell density where such comparison provides a relative sample cell density. The relative sample cell density may be determined by comparing the measured cell density of the sample to a measured cell density of a control or reference value, e.g., a known healthy control or reference or a known tumor control or reference. For example, the determined relative sample cell density may be indicative of a tumor sample when the relative sample cell density of the sample is greater than or equal to (≥) 2 times the sample cell density of a healthy reference or control, including but not limited to, e.g., ≥2.1 times, ≥2.2 times, ≥2.3 times, ≥2.4 times, ≥2.5 times, ≥2.6 times, ≥2.7 times, ≥2.8 times, ≥2.9 times, ≥3.0 times, ≥3.1 times, ≥3.2 times, ≥3.3 times, ≥3.4 times, ≥3.5 times, ≥3.6 times, ≥3.7 times, ≥3.8 times, ≥3.9 times, ≥4.0 times, ≥4.1 times, ≥4.2 times, ≥4.3 times, ≥4.4 times, ≥4.5 times, ≥4.6 times, ≥4.7 times, ≥4.8 times, ≥4.9 times, ≥5.0 times, ≥5.1 times, ≥5.2 times, ≥5.3 times, ≥5.4 times and ≥5.5 times the sample cell density of a healthy reference or control.

In some instances, obtained sample data may be evaluated in comparison to a pre-determined sample cell density of a known metastatic tumor sample ranging from less than 200,000 to 1,000,000 cells per volume of analyzed sample, e.g., 300 µl of analyzed sample, or more including but not limited to, e.g., 200,000 cells per 300 µl of analyzed sample, 250,000 cells per 300 µl of analyzed sample, 300,000 cells per 300 µl of analyzed sample, 450,000 cells per 300 µl of analyzed sample, 500,000 cells per 300 µl of analyzed sample, 550,000 cells per 300 µl of analyzed sample, 600,000 cells per 300 µl of analyzed sample, 650,000 cells per 300 µl of analyzed sample, 700,000 cells per 300 µl of analyzed sample, 750,000 cells per 300 µl of analyzed sample, 800,000 cells per 300 µl of analyzed sample, 850,000 cells per 300 µl of analyzed sample, 900,000 cells per 300 µl of analyzed sample, 950,000 cells per 300 µl of analyzed sample, 1,000,000 cells per 300 µl of analyzed sample, etc. In some instances, the pre-determined sample cell density data parameter may be a sample cell density threshold indicative of a metastatic tumor sample where a sample cell density at or above the threshold indicates a likelihood that the sample is a metastatic tumor sample. For example, a sample cell density threshold indicative of a metastatic tumor sample may include but is not limited to a sample cell density of 200,000 or more cells per volume of analyzed sample, e.g., 300 µl of analyzed sample, including but not limited to, e.g., 250,000 or more cells per 300 µl of analyzed sample, 300,000 or more cells per 300 µl of analyzed sample, 350,000 or more cells per 300 µl of analyzed sample, 400,000 or more cells per 300 µl of analyzed sample, 450,000 or more cells per 300 µl of analyzed sample, 500,000 or more cells per 300 µl of analyzed sample, 550,000 or more cells per 300 µl of analyzed sample, 600,000 or more cells per 300 µl of analyzed sample, 650,000 or more cells per 300 µl of analyzed sample, 700,000 or more cells per 300 µl of analyzed sample, 750,000 or more cells per 300 µl of analyzed sample, 800,000 or more cells per 300 µl of analyzed sample, 850,000 or more cells per 300 µl of analyzed sample, etc. In comparing the sample cell density of samples, e.g., in order to determine whether a tumor sample is a metastatic tumor sample, any convenient measure of sample cell density may be employed including but not limited to single cell counts, epithelial cell counts, etc.

In some instances, obtained sample data may be evaluated in comparison to a pre-determined sample cell density where such comparison provides a relative sample cell density. The relative sample cell density may be determined by comparing the measured cell density of the sample to a measured cell density of a control or reference value, e.g., a known tumor control or reference or a known metastatic tumor control or reference. For example, the determined relative sample cell density may be indicative of a metastatic tumor sample when the relative sample cell density of the sample is greater than or equal to (≥) 2 times the sample cell density of a non-metastatic tumor reference or control sample, including but not limited to, e.g., ≥2.5 times, ≥3.0 times, ≥3.5 times, ≥4.0 times, ≥4.5 times, ≥5.0 times, ≥5.5 times, ≥6.0 times, ≥6.5 times, ≥7.0 times, ≥7.5 times, ≥8.0 times, ≥8.5 times, ≥9.0 times, ≥9.5 times, ≥10.0 times, ≥10.5 times, ≥11.0 times, ≥11.5 times, ≥12.0 times, ≥12.5 times, ≥13.0 times, ≥13.5 times, ≥14.0 times, ≥14.5 times, ≥15.0 times, ≥15.5 times, ≥16.0 times, ≥16.5 times, ≥17.0 times, ≥17.5 times, ≥18.0 times, ≥18.5 times, ≥19.0 times, ≥19.5 times, ≥20.0 times, ≥20.5 times and ≥21.0 times the sample cell density of a non-metastatic tumor reference or control sample.

In some instances, evaluations of obtained cellular data may be based on pre-determined cellular data parameters. Pre-determined cellular data parameters may be reference values (e.g., reference values provided for comparison to obtained experimental values) or pre-determined cellular data may be user-defined (e.g., through measuring a cellular data parameter of the cells of a control sample (e.g., a healthy control, a cancerous control, or other reference control and combinations thereof) or a control subpopulation of the sample (e.g., a gated subpopulation). Pre-determined cellular data parameters may be provided or user-defined for any cellular data, e.g., including those described herein.

In some instances, pre-determined cellular data parameters may include per cell DNA content parameters, e.g., epithelial cell per cell DNA content parameters. For example, in some instances, obtained cellular data may be evaluated in comparison to a pre-determined per cell DNA content parameter calculated or previously obtained for a normal epithelial cell or normal non-epithelial cell type of the sample, including but not limited to e.g., a WBC of the sample. As such, in some instances, the measured DNA content, e.g., the mean DNA content of the cells of the sample or a subpopulation of cells of the sample (e.g., the epithelial cells of the sample), may be compared to the pre-determined per cell DNA content parameter to arrive at a relative per cell DNA content value for the subject cells or subject subpopulation of cells. In some instances, a relative per cell DNA content value for the cells of the sample, or subpopulation thereof, may be above a particular threshold that indicates that the sample has an increased likelihood of being a tumor sample. For example, a relative DNA content greater than or equal to a threshold DNA content value for a normal cell may indicate that the sample has an increased likelihood of being a tumor sample where the threshold may be greater than or equal to (≥) 1.05 times the DNA content of a normal cell including but not limited to, e.g., ≥1.06 times, ≥1.07 times, ≥1.08 times, ≥1.09 times, ≥1.10 times, ≥1.11 times, ≥1.12 times and ≥1.13 times the DNA content of a normal cell.

In some instances, obtained cellular data may be evaluated in comparison to a pre-determined per cell DNA content parameter calculated or previously obtained for a tumor cell of the sample. As such, in some instances, the measured DNA content, e.g., the mean DNA content of the cells of the sample or a subpopulation of cells of the sample (e.g., the epithelial cells of the sample), may be compared to a pre-determined per cell DNA content parameter of tumor cells to arrive at a relative per cell DNA content value for the subject cells or subject subpopulation of cells that is relative to tumor cells, e.g., non-metastatic tumor cells or metastatic tumor cells. In some instances, a relative per cell DNA content value for the cells of the sample, or subpopulation thereof, may be above a particular threshold that indicates that the sample has an increased likelihood of being a metastatic tumor sample. For example, a relative DNA content greater than or equal to a threshold DNA content value for a non-metastatic tumor cell may indicate that the sample has an increased likelihood of being a metastatic tumor sample where the threshold may be greater than or equal to (≥) 1.05 times the DNA content of a non-metastatic tumor cell including but not limited to, e.g., ≥1.06 times, ≥1.07 times, ≥1.08 times, ≥1.09 times, ≥1.10 times, ≥1.11 times, ≥1.12 times, ≥1.13 times, ≥1.14 times, and ≥1.15 times the DNA content of a non-metastatic tumor cell.

In some instances, pre-determined cellular data parameters may include cell proliferation parameters, e.g., epithelial cell proliferation parameters. For example, in some instances, obtained cellular data may be evaluated in comparison to a pre-determined cell proliferation percentage for a healthy sample where the proliferation percentage may be expressed as the percentage of cells, e.g., epithelial cells, in a particular phase of the cell cycle (e.g., $G_1$, S, $G_2$, M, etc.) or cell cycle phases other than the $G_1$ phase of the cell cycle (e.g., "post-$G_1$"). In some instances, the epithelial cell proliferation parameter for epithelial cells of a healthy sample will be 15% or less (e.g., where 15% of the cells are in post-$G_1$ and 85% of cells are in $G_1$ phase) including but not limited to, e.g., 14% or less, 13% or less, 12% or less, 11% or less, 10% or less, 9.5% or less, 9.0% or less, 8.5% or less, 8.0% or less and 7.5% or less. In some instances, the epithelial cell proliferation parameter for epithelial cells of a tumor sample will be 20% or more (e.g., where 20% of the cells are in post-$G_1$ and 80% of the cells are in $G_1$ phase) including but not limited to, e.g., 20.5% or more, 21.0% or more, 21.5% or more, 22.0% or more, 22.5% or more, 23.0% or more, 23.5% or more and 24.0% or more. In some instances, a relative proliferation percentage greater than or equal to a pre-determined threshold proliferation percentage for a healthy sample may indicate that the subject sample has an increased likelihood of being a tumor sample where the threshold may be greater than or equal to (≥) 1.1 times the proliferation percentage of the healthy sample including but not limited to, e.g., ≥1.2 times, ≥1.3 times, ≥1.4 times, ≥1.5 times, ≥1.6 times, ≥1.7 times, ≥1.8 times, ≥1.9 times, ≥2.0 times, ≥2.1 times, ≥2.2 times, ≥2.3 times, ≥2.4 times, ≥2.5 times, ≥2.6 times, ≥2.7 times and ≥2.8 times the proliferation percentage of the healthy sample.

In some instances, pre-determined cellular data parameters may include per cell biomarker expression parameters, e.g., epithelial per cell biomarker expression parameters. For example, in some instances, obtained cellular data may be evaluated in comparison to a pre-determined epithelial per cell biomarker expression value conveyed as mean fluorescence intensity or median mean fluorescence intensity. For example, in some instances, obtained biomarker expression data may be evaluated in comparison to a pre-determined per cell biomarker expression parameter calculated or previously obtained for epithelial cells of a non-metastatic tumor sample including but not limited to, e.g., the mean fluorescence intensity (MFI) of Her2 biomarker probe for the epithelial cells of a non-metastatic tumor sample. As such, in some instances, the measured Her2 MFI, e.g., the mean Her2 MFI of the cells of the sample or a subpopulation of cells of the sample (e.g., the epithelial cells of the sample), may be compared to the pre-determined per cell Her2 MFI parameter to arrive at a relative per cell Her2 MFI value for the subject cells or subject subpopulation of cells. In some instances, a relative per cell Her2 MFI value for the cells of the sample, or subpopulation thereof, may be above a particular threshold that indicates that the sample has an increased likelihood of being a metastatic tumor sample. For example, a relative Her2 MFI greater than or equal to a threshold Her2 MFI value for a non-metastatic tumor sample may indicate that the sample has an increased likelihood of being a metastatic tumor sample where the threshold may be greater than or equal to (≥) 1.50 times the Her2 MFI of the non-metastatic tumor sample including but not limited to, e.g., ≥1.75 times, ≥2.0 times, ≥2.1 times, ≥2.2 times, ≥2.3 times, ≥2.4 times, ≥2.5 times, ≥2.6 times and ≥2.7 times the Her2 MFI of the non-metastatic tumor sample.

In some instances, pre-determined cellular data parameters may include per cell volume parameters, e.g., epithelial per cell volume parameters. For example, in some instances, obtained cellular data may be evaluated in comparison to a pre-determined epithelial per cell volume expressed as mean corpuscular volume (MCV) or median MCV. For example, in some instances, obtained cell volume data may be evaluated in comparison to a pre-determined per cell volume parameter calculated or previously obtained for epithelial cells of a healthy sample including but not limited to, e.g., the median MCV for the epithelial cells of a healthy sample. As such, in some instances, the measured cell volumes of the sample may be compared to the pre-determined cell volume parameter to arrive at a relative cell volume value for the subject cells or subject subpopulation of cells. In some instances, a relative cell volume value for the cells of the sample, or subpopulation thereof, may be above a particular threshold that indicates that the sample has an increased likelihood of being a tumor sample. For example, a relative cell volume value greater than or equal to a threshold cell volume parameter for a healthy sample may indicate that the sample has an increased likelihood of being a tumor sample where the threshold may be greater than or equal to (≥) 1.50 times the cell volume parameter for a healthy sample including but not limited to, e.g., ≥1.55 times, ≥1.60 times, ≥1.65 times, ≥1.70 times, ≥1.75 times, ≥1.80 times and ≥1.85 times the cell volume parameter for a healthy sample.

In some instances, a relative cell volume value for the cells of the sample, or subpopulation thereof, may be above a particular threshold that indicates that the sample has an increased likelihood of being a metastatic tumor sample. For example, a relative cell volume value less than or equal to a threshold cell volume parameter for a non-metastatic tumor sample may indicate that the sample has an increased likelihood of being a metastatic tumor sample where the threshold may be less than or equal to (≤) 0.75 times the cell volume parameter for a non-metastatic tumor sample including but not limited to, e.g., ≤0.70 times, ≤0.65 times, ≤0.60 times, ≤0.55 times and ≤0.50 times the cell volume parameter for a non-metastatic tumor sample.

In some instances, pre-determined cellular data parameters may include WBC parameters, e.g., WBC background biomarker signal parameters, WBC proliferation parameters, etc. For example, in some instances, obtained WBC cellular data may be evaluated in comparison to a pre-determined background biomarker signal, e.g., background ER biomarker signal in WBCs, background PR biomarker signal in WBCs, background combination ER/PR biomarker signal in WBCs, etc., where the pre-determined background biomarker signal may be the mean fluorescence of the biomarker or the median fluorescence of the biomarker in the WBCs or a subpopulation of WBCs. In some instances, a relative WBC background biomarker signal in a sample less than or equal to a pre-determined threshold WBC background biomarker signal for a healthy sample may indicate that the subject sample has an increased likelihood of being a tumor sample where the threshold may be less than or equal to (≤) 0.95 times the WBC background biomarker signal of the healthy sample including but not limited to, e.g., ≤0.94 times, ≤0.93 times, ≤0.92 times, ≤0.91 times, ≤0.90 times, ≤0.89 times, ≤0.88 times, ≤0.87 times, ≤0.86 times, ≤0.85 times, ≤0.84 times, ≤0.83 times, ≤0.82 times, ≤0.81 times and ≤0.80 times the WBC background biomarker signal of the healthy sample.

In some instances, obtained WBC sample data may be evaluated in comparison to a pre-determined WBC sample parameter. For example, in some instances, obtained WBC sample data, e.g., the percentage of WBCs in the sample, may be evaluated in comparison to a pre-determined WBC sample parameter, e.g., the percentage of WBCs in the sample. In some instances, the percent WBC sample parameter for a non-metastatic tumor sample will be 17% or more including but not limited to, e.g., 18% or more, 19% or more, 20% or more, 21% or more, 22% or more and 23% or more. In some instances, the percent WBC sample parameter for a metastatic tumor sample will be 15% or less including but not limited to, e.g., 14% or less, 13% or less, 12% or less, 11% or less, 10% or less and 9% or less. In some instances, a relative percentage of WBCs in the sample less than or equal to a pre-determined threshold percentage of WBCs for a non-metastatic tumor sample may indicate that the subject sample has an increased likelihood of being a metastatic tumor sample where the threshold may be less than or equal to (s) 0.70 times the percentage of WBCs of the non-metastatic tumor sample including but not limited to, e.g., ≤0.65 times, ≤0.60 times, ≤0.55 times, ≤0.50 times, ≤0.45 times and ≤0.40 times the percentage of WBCs of the non-metastatic tumor sample.

Parameters useful in evaluating obtained data are not limited to those specifically described above. Useful parameters for any data type, including the sample data and cellular data as described herein, for performing assessments of cellular breast samples may be readily determined according to the described methods, including but not limited to flow cytometrically assaying control samples, e.g., control healthy samples and/or control tumor samples, for the particular data. In some instances, useful data parameters may be determined by performing statistical analysis of acquired data including but not limited to the statistical testing methods described herein. In some instances, useful data parameters may be determined by performing statistical analysis of two or more acquired data types including but not limited to multivariate statistical analysis and multivariate statistical modeling.

Combinations of useful parameters may be determined by evaluating a known training set of samples (e.g., a training set of samples containing known healthy samples and known cancer samples) or sample data (e.g., a training set of data from known healthy samples and known cancer samples) to build a multi-parameter statistical model capable of classifying a sample as cancerous or non-cancerous. In some instances, the model may be built based on a desired number of parameters. The number of parameters in a multi-parameter model will vary depending on whether the model is constrained to a predetermined or desired number of parameters or whether the number of parameters within the model are not constrained and allowed to vary in determining the best or most efficient parameter set. The number of parameters in a multi-parameter model will vary and may range from 2 to 20 or more including but not limited to e.g., 2 to 20, 2 to 15, 2 to 14, 2 to 13, 2 to 12, 2 to 11, 2 to 10, 2 to 9, 2 to 8, 2 to 7, 2 to 6, 2 to 5, 2 to 4, 3 to 20, 3 to 15, 3 to 14, 3 to 13, 3 to 12, 3 to 11, 3 to 10, 3 to 9, 3 to 8, 3 to 7, 3 to 6, 3 to 5, 4 to 20, 4 to 15, 4 to 14, 4 to 13, 4 to 12, 4 to 11, 4 to 10, 4 to 9, 4 to 8, 4 to 7, 4 to 6, 5 to 20, 5 to 15, 5 to 14, 5 to 13, 5 to 12, 5 to 11, 5 to 10, 5 to 9, 5 to 8, 5 to 7, 10 to 20, 15 to 20, 2, 3, 4, 5, 6, 7, 8, 9, 10, 11, 12, 13, 14, 15, etc.

In some instances, the parameters of a multi-parameter model may be determined based on inputting a training set of data into a linear regression model and determining the parameter set(s) capable of classifying samples as cancerous or non-cancerous with a desired specificity and/or sensitivity. The desired level of sensitivity and/or specificity will vary and may range from, e.g., at least 80% or greater including but not limited to e.g., at least 80%, at least 85%, at least 90%, at least 95%, etc. In some instances, both the sensitivity and specificity are at least 80%, including but not limited to e.g., at least 85%, at least 90%, at least 95%, etc. The sensitive and/or specificity of a multi-parameter model may be tested on known samples to confirm or verify the sensitivity and/or specificity of the model on samples and/or data different from that of the training set from which it was developed.

Assessments

As summarized above, aspects of the instant disclosure are directed to making an assessment of a cellular breast sample from a subject based on evaluation of data obtained from the sample. The terms "subject", "individual", and "patient," are used interchangeably herein and refer to any mammalian subject for whom diagnosis, treatment, or therapy is desired, and in some instances include humans.

In some instances, the assessment includes assessing the presence of a neoplastic disease in a subject, i.e., a judgment or appraisal of whether or not a subject suffers from a neoplastic disease. As used herein the term "neoplastic disease" refers to diseases and conditions characterized by abnormal tissue growth, including cancer. In aspects of the instant disclosure neoplastic disease assessments include breast cancer assessments where the term "breast cancer" as used herein generally includes neoplastic diseases of the breast tissue including but not limited to, e.g., pre-cancers, cancers in situ, invasive cancers, carcinomas, sarcomas, adenocarcinomas, ductal carcinoma, ductal carcinoma in situ, invasive ductal carcinoma, lobular carcinoma, invasive lobular carcinoma, inflammatory breast cancer, Paget disease, Phyllodes tumor, angiosarcoma, adenoid cystic carcinoma, low-grade adenosquamous carcinoma, medullary carcinoma, mucinous (or colloid) carcinoma, papillary carcinoma, tubular carcinoma, metaplastic carcinoma, micropapillary carcinoma, mixed carcinoma (e.g., having features of both invasive ductal and lobular), and the like.

In some instances, the individual has a clinically insignificant amount of breast neoplasia, or does not suffer from breast cancer. For example, assessments of the present disclosure find use in breast neoplasia surveillance of individuals not at an increased risk of developing breast neoplasia or breast cancer, e.g., healthy individuals or individuals that have not previously had a positive breast cancer screening test, i.e., a breast cancer screening test that indicated the presence of a breast neoplasia.

In some instances, the individual has a clinically significant amount of breast neoplasia, i.e., an above-average amount of breast neoplasia compared to a healthy individual, e.g., due to any syndrome or cause that increases breast cancer formation. For example, assessments of the present disclosure find use in breast cancer surveillance of individuals with increased rates of breast cancer, e.g., assessments may be used for breast cancer surveillance in individuals with breast cancer.

In some instances, the individual has an increased risk of developing breast cancer. Such individuals may have an increased risk of breast cancer due to the presence of any known risk factor, e.g., family medical history or a positive screening test (e.g., including breast cancer genetic tests) or prior presence of breast cancer or prior removal or treatment of breast cancer. Other such factors that increase the risk of breast cancer include, but are not limited to, female gender, increasing age (e.g., over 45 years of age, over 55 years of age, etc.), presence of genetic mutation in a breast cancer related gene (e.g., mutation in BRCA1, mutation in BRCA2, mutation in ATM, mutation in TP53, mutation in CHEK2, mutation in PTEN, mutation in CDH1, mutation in STK11, mutation in PALB2, etc.), presence of genetic mutation in cancer related gene, family history of breast cancer, personal history of breast cancer, Caucasian race, African-American race, high breast tissue density (e.g., high ratio of glandular tissue and/or fibrous tissue to fatty tissue), post-menopausal status, menopausal hormone therapy, presence of non-proliferative lesions (e.g., fibrosis, cysts, mild hyperplasia, non-sclerosing adenosis, ductal ectasia, benign Phyllodes tumor, single papilloma, fat necrosis, periductal fibrosis, squamous metaplasia, apocrine metaplasia, epithelial-related calcifications, lipoma, hamartoma, hemangioma, neurofibroma, adenomyoepthelioma, etc.), proliferative lesions without atypia (e.g., ductal hyperplasia, fibroadenoma, sclerosing adenosis, papillomatosis, radial scar, etc.), proliferative lesions with atypia (e.g., atypical ductal hyperplasia (ADH), atypical lobular hyperplasia (ALH), etc.), presence of lobular carcinoma in situ, increased life-time exposure to estrogen and progesterone (e.g., early start of menstruation, late start of menopause, etc.), increased chest exposure to radiation (e.g., radiation therapy to the chest area, etc.), increased diethylstilbestrol exposure, having children, having children after 30 years of age, taking oral contraceptives, drinking alcohol, being overweight, obesity, etc.

In certain instances, increased surveillance of breast cancer in an individual, according to the methods described herein, is indicated when the individual has a single risk factor for breast cancer. In certain instances, increased surveillance of breast cancer in an individual, according to the methods described herein, is indicated when the individual has multiple, e.g., more than one, e.g., about 2-5, e.g., about 2, about 3, about 4, or about 5, risk factors for breast cancer. In certain instances, increased surveillance of breast cancer in an individual, according to the methods described herein, is indicated when the individual has a single or combined relative risk, as calculated by any convenient method of calculating relative risk from a single risk factor or multiple risk factors, of equal to or greater than about 1.1, e.g., from about 1.1 to about 1.4, from about 1.3 to about 2.0, greater than about 2.0, greater than about 2.5, greater than about 3, greater than about 4, greater than about 5, greater than about 7.5, greater than about 10, greater than about 15, greater than about 20, and the like, optionally with a maximum of about 200. Relative risk for particular single risk factors or multiple risk factors in breast cancer may, in some instances, include those described in, e.g., Singletary, S. E. (2003) *Ann Surg.* 237(4): 474-482, the disclosure of which is incorporated herein by reference in its entirety.

By increased surveillance is meant increased screening at a frequency greater than that recommended for comparable (e.g., age matched, gender matched, race matched, etc.) healthy individuals. In certain embodiments, increased surveillance may be performed at more than about 1.5 to 5 times the breast cancer screening frequency recommended for comparable healthy individuals where increased surveillance is not indicated e.g., about 1.5 to 2 times the normal frequency, about 2 to 3 times the normal frequency, about 3 to 4 times the normal frequency, or about 4 to 5 times the normal frequency. In certain instances increased surveillance calls for triennial, biennial, annual, semiannual, triannual, or quarterly assessments.

In some instances, surveillance may be performed on subject known to have a breast neoplasia, e.g., in order to assess the malignancy of a subject's breast neoplasia, e.g., to determine whether the subject has metastatic breast cancer. Increased surveillance may be performed, as described above, in subjects with increased risk of developing metastatic breast cancer. In some instances, surveillance of the malignancy of a subject's breast neoplasia may be begun after identification and/or detection of a breast neoplasia in a subject and continued for a period of time ranging from 6 month or more including but not limited to, e.g., 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, etc. and/or indefinitely. The frequency of malignancy surveillance assessments for a particular subject will vary depending on the particular breast neoplasia present in the subject including but not limited to, e.g., triennial, biennial, annual, semiannual, triannual, or quarterly, etc.

In some instances, an assessment as described herein includes both an assessment of the presence of a breast neoplasia and an assessment of the malignancy of a detected breast neoplasia. For example, data obtained from a single cellular sample obtained from a subject may be evaluated according to the method as described herein and from the evaluation an assessment may be made to determine if the subject has a breast neoplasia and, if so, whether the breast neoplasia is or is not metastatic. In other instances, a breast neoplasia assessment made from a first patient sample indicating the presence of a breast neoplasia may indicate the necessity to obtain one or more additional samples from the subject for additional testing, e.g., malignancy testing, confirmatory testing, etc.

In some instances, an assessment as described herein may include a comparison or correlation with known slide-based cytological grading systems for breast carcinoma including but not limited to, e.g., Fisher's, Mouriquand's, Robinson's, Howell's, Khan's, Taniguchi's, etc. Such grading systems generally make use of Papanicolaou (Pap) stained FNA smears and make use of cellular characteristics, nuclear features, and have been described, e.g., in Saha et al. (2013) *J. Cytol.* 30(2):87-93, the disclosure of which is incorporated herein by reference in its entirety. In some instances, an assessment as described herein may include a comparison or correlation with known slide-based histological grading systems for breast carcinoma including but not limited to, e.g., Scarff-Bloom-Richardson system, Nottingham histological grade (NHG), and the like.

In some instances, the methods further include performing further analysis of a subject if the methods result in an assessment (e.g., judgment or appraisal (such as in the form of a prediction)) of a breast neoplasia in the subject or an assessment of metastatic breast cancer in the subject. For example, where methods of the invention result in an assessment of a breast neoplasia in a subject or metastatic breast cancer in the subject, the methods may then further include providing a recommendation to a subject that further action be taken, e.g., in the form of further diagnostic procedures, such as biopsy or further biopsy. In some instances, the methods include taking further diagnostic action. Further diagnostic action may include but is not limited to a core biopsy or surgical biopsy, as described herein. If the biopsy indicates that cancer or pre-cancerous lesions or metastatic breast cancer in the subject may be present, further diagnostic and treatment procedures may be taken, such as partial or total mastectomy, in which the a portion or the entire breast is removed and may or may not be further examined pathologically.

In some embodiments, providing a breast neoplasia assessment of, e.g., in the form of a judgment or appraisal of the presence of, and in some instances a diagnosis of, breast cancer (an in some instances metastatic breast cancer), determining a therapy for a subject having breast cancer, monitoring a subject having breast cancer, etc. includes generating a written report that includes the artisan's assessment of the subject's current state of health i.e., a "diagnosis assessment", of the subject's prognosis, i.e., a "prognosis assessment", of possible treatment regimens, i.e., a "treatment assessment" and/or of responsiveness to therapy, i.e., a "prognosis assessment". Thus, a subject method may further include a step of generating or outputting a report providing the results of a diagnosis assessment, a prognosis assessment, treatment assessment, or a monitoring assessment, and combinations thereof, which report can be provided in the form of an electronic medium (e.g., an electronic display on a computer monitor), or in the form of a tangible medium (e.g., a report printed on paper or other tangible medium).

In some instances, assessments as described herein are performed as part of a treatment regimen, e.g., to assess the effectiveness of treatment or to determine the best timing of treatment or to determine whether modulation of treatment is necessary. For, example, in some instances a pretreatment sample may be collected and assessed according to the methods described herein and from the assessment a treatment protocol is selected. In other instances, a post-treatment sample is collected and compared, according to the assessments described herein, to a pre-treatment sample in order to evaluate treatment effectiveness. In other instances, one or more post treatment assessments are performed to best determine the timing of further therapy. For example, assessments as described herein may be performed as part of a (e.g., before, during, and/or after) neoadjuvant therapy where neoadjuvant therapy is performed as to reduce the tumor before primary treatment. In one embodiment surgery is performed and one or more assessments are performed following surgery to determine the course of further therapy, e.g., chemotherapy, radiation therapy, hormone therapy, additional surgery, etc.

In some instances, the assessment of the cellular breast sample is made within a short period of time following introduction of the sample into the cytometer. Accordingly, results may be provided to a user in a period of 6 hours or less, such as 3 hours or less, e.g., 2 hours or less, including 1 hour or less, optionally including a minimum of the time necessary to process the sample or a sufficient portion of the sample through the cytometer to make the assessment including but not limited to, e.g., 5 min, 10 min., 20 min., and 30 min. Where desired, the overall assay time which ranges from obtainment of the sample from the subject to delivery of the result to the subject is 6 hours or less, such as 5 hours or less, e.g., 4 hours less, including 3 hours or less, e.g., 2 hours or less, optionally including a minimum of the time necessary to physically collect the sample and process the sample or a sufficient portion of the sample including but not limited to, e.g., 30 min., 45 min., and 1 hour.

Kits

In yet another aspect, the present invention provides kits for practicing the subject methods, e.g., as described above. The subject kits may include any combination of the above described reagents, devices, or systems useful in practicing the methods as described above including but not limited to, e.g., one or more of the described specific binding agents or labels. Subject kits may further include one or more sample preparation reagents including but not limited to, e.g., cell fixatives, cell permeabilizing reagents, cell labeling reagents, buffers, diluents, etc. The above components may be present in separate containers or one or more components may be combined into a single container, e.g., a glass or plastic vial.

Kits may further include sample obtainment devices, e.g., needle biopsy devices, core biopsy devices, punch biopsy devices, surgical biopsy devices, vacuum assisted biopsy devices, etc. In some instances, kits may further include one or more reagents and/or devices for cell dissociation including but not limited to e.g., enzymes, enzyme inhibitors, detergents, cell dissociation media or buffer, vortex devices, nutating devices, rocking devices, etc. Subject kits may further include control reagents and samples including but not limited to, e.g., control cell samples (e.g., positive control cellular samples, negative control cellular samples, etc.) calibration reagents (e.g., fluorescent beads, pre-labeled cells, etc.).

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, removable drive (e.g., flash memory device), etc., on which the information has been recorded. Yet another means that may be present is a website address which may be used via the internet to access the information at a removed site. Any convenient means may be present in the kits.

Systems

Aspects of the invention further include systems for use in practicing the subject methods. Systems of interest include a flow cytometer configured to assay a liquid sample for both sample data and cellular data, e.g., as described above. Flow cytometry systems of interest include, e.g., those available from commercial suppliers including but not limited to, e.g., Becton-Dickenson (Franklin Lakes, N.J.), Life Technologies (Grand Island, N.Y.), Acea Biosciences (San Diego, Calif.), Beckman-Coulter, Inc. (Indianapolis, Ind.), Bio-Rad Laboratories, Inc. (Hercules, Calif.), Cytonome, Inc. (Boston, Mass.), Amnis Corporation (Seattle, Wash.), EMD Millipore (Billerica, Mass.), Sony Biotechnology, Inc. (San Jose, Calif.), Stratedigm Corporation (San Jose, Calif.), Union Biometrica, Inc. (Holliston, Mass.), Cytek Development (Fremont, Calif.), Propel Labs, Inc. (Fort Collins, Colo.), Orflow Technologies (Ketchum, Id.), handyem inc. (Québec, Canada), Sysmex Corporation (Kobe, Japan), Partec Japan, Inc. (Tsuchiura, Japan), Bay bioscience (Kobe, Japan), Furukawa Electric Co. Ltd. (Tokyo, Japan), On-chip Biotechnologies Co., Ltd (Tokyo, Japan), Apogee Flow Systems Ltd. (Hertfordshire, United Kingdom), and the like.

In some instances, the flow cytometer includes: a flow channel; at least a first light source configured to direct light to an assay region of the flow channel (where in some instances the cytometer includes two or more light sources); one or more detectors configured to receive light of a first emission wavelength from the assay region of the flow channel and light of a second emission wavelength from the assay region of the flow channel; and an electrical detector configured to measure cell volume by detecting changes in an electrical current caused by a cell of the sample in the assay region. Such a cytometer would have at least one detection channel in addition to the electrical detector. In some instances, the device may include more than one detection channel, e.g., 2 or more, 3 or more, 4 or more, 5 or more, or more, etc.

Aspects of the invention further include a signal processing module configured to receive the sample data and cellular data from the one or more detectors and the electrical detector to output a result of an assessment of whether a subject has a breast neoplasia or metastatic breast cancer based on both the sample data and the cellular data. The signal processing module may be integrated into the cytometer as a single device, or distributed from the cytometer where the signal processing module and cytometer are in communication with each other, e.g., via a wired or wireless communication protocol.

Accordingly, aspects of the invention further include systems, e.g., computer based systems, which are configured to predict the presence of a breast neoplasia or metastatic breast cancer in a subject, e.g., as described above. A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g., word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Embodiments of the subject systems include the following components: (a) a communications module for facilitating information transfer between the system and one or more users, e.g., via a user computer, as described below; and (b) a processing module for performing one or more tasks involved in the quantitative analysis methods of the invention.

In certain embodiments, a computer program product is described comprising a computer usable medium having control logic (computer software program, including program code) stored therein. The control logic, when executed by the processor of the computer, causes the processor to perform functions described herein. In other embodiments, some functions are implemented primarily in hardware using, for example, a hardware state machine. Implementation of the hardware state machine so as to perform the functions described herein may be accomplished using any convenient method and techniques.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

In some instances, the systems may further include a reaction mixture derivative thereof (e.g., washed cells produced therefrom), where the reaction mixture is prepared as described above, e.g., by combining a sample, one or more detectable specific binding agents and, optional, an additional label.

Utility

Assessments of cellular breast samples as described herein find use in a variety of applications. Such assessments are useful in acquiring sample data and/or cellular data that may be used in making determinations pertaining to the sample and/or the cells of the sample. Samples that may be assessed according to the methods described herein have been described in detail above and generally include laboratory research samples (e.g., those described for non-clinical research use), clinical research samples, patient samples, diagnostic samples, prognostic samples, treatment samples, and the like. The combined data of the described sample evaluations are useful in comparing samples to one another, e.g., as in the comparison of two research samples (e.g., two research samples treated with two different experimental agents), comparison of an experimental sample to a control (e.g., comparison of an treated sample to an untreated control) and in comparing samples to a reference (e.g., a control reference or a reference value such as a healthy or cancer sample or a healthy or cancer level).

As described above, assessments based on the collected data find use detecting neoplastic cells and in making assessments of whether a subject has a neoplastic lesion and/or predicting the malignancy of a detected lesion. Without being bound by theory, the assessments based on various factors of combined sample data and cellular data, as described herein, leverage the multimodal developmental causes of breast cancer to aid in cancer detection and/or identification of metastatic disease.

The assessments described herein find use in screening of subjects for disease, either as a first-line of detection in suspected healthy individuals and/or as a surveillance mechanism for those at increased risk of developing neoplastic disease or metastatic disease. The assessments may be performed independently or combined with conventional routine screening and biopsy advancing the rate of detection, reducing the rate of false negative and false positive assessments, and generally improving the standard of care related to breast cancer detection, monitoring, and treatment.

In addition to the above described patient assessments, the assessments described also find use in the research setting in evaluation of obtained sample data from laboratory, pre-clinical, and clinical models of breast cancer development and treatment. For example, owing to the cellular nature of the described method, xenografts (e.g., human derived xenografts) may be assayed directly from a host animal and evaluated according to the methods described herein, e.g., as a method of studying breast cancer development in such models with direct clinical relevancy. Such xenografts and/or other animal models of cancer, including but not limited to breast cancer, can also be studied under experimental treatment regimens or agents which utilize the assessments described herein as a method to assay the effectiveness of such treatment regimens or agents. Furthermore, given the non-subjective and unbiased approach of the cellular assessments described herein, the described methods also find use in combination with clinical research, e.g., in evaluating pre- and post-treatment samples for treatment effectiveness and/or monitoring treatment effectiveness during testing through one or more assessments during the course of a clinical trial.

The above described uses are in no way to be considered limiting as the methods and systems described herein may have additional utility not described herein.

Computer Related Embodiments

Aspects of the invention further include a variety of computer-related embodiments. Specifically, the data analysis methods described in the previous sections may be performed using a computer. Accordingly, the invention provides a computer-based system for analyzing data produced using the above methods in order to make a breast neoplasia assessment or metastatic breast cancer assessment.

In certain embodiments, the methods are coded onto a physical computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. Of interest as media are non-transitory media, i.e., physical media in which the programming is associated with, such as recorded onto, a physical structure. Non-transitory media does not include electronic signals in transit via a wireless protocol.

With respect to computer readable media, "permanent memory" refers to memory that is permanent. Permanent memory is not erased by termination of the electrical supply to a computer or processor. Computer hard-drive, CD-ROM, floppy disk and DVD are all examples of permanent memory. Random Access Memory (RAM) is an example of non-permanent memory. A file in permanent memory may be editable and re-writable.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents and devices referred to in this disclosure are available from commercial vendors such as Abcam, Biolengend, Life Technologies, Sigma-Aldrich, CST, Biosearch, Sony Biotechnology and others.

Example 1

Calibration

Prior to performing flow cytometric assays the flow cytometer (Sony Biotechnology EC800 spec) was calibrated such that: (1) the Align Check beads achieved a HPCV (half peak CV) of less than 2.5% in all collected parameters, (2) the 8 peak rainbow beads demonstrated 8 distinct peaks in FL1, FL2, FL3, FL4 and FL5, and (3) the 6 peak beads demonstrated 6 distinct peaks in FL3 and FL4.

Materials

The following antibodies and probes were utilized in Example 1:

| Antibody/Probe | Commercial Source | Part # | Clone |
|---|---|---|---|
| ER-alpha (estrogen receptor alpha) | Abcam | ab79413 | EPR703(2) |
| PR (progesterone receptor) | Abcam | ab32085 | Y85 |
| E-cadherin | Abcam | ab40772 | EP700Y |
| Anti-HER2 PE | Biolegend | 324406 | 24D2 |
| CD45 PE/Cy7 | Biolegend | 304016 | HI30 |
| CD44-PE | Life Technologies | MHCD4404 | MEM-85 |
| Vimentin PE | CST | 12020 | D21H3 |
| p-H2A.X Alexa 647 | CST | 9720 | Ser139 |
| Cleaved Caspase 3 Alexa 488 | CST | 9603 | Asp175, D3E9 |
| Anti-Rabbit IgG Alexa 647 | Life Technologies | A-21246 | F(ab')2 |
| DAPI | Invitrogen | D1306 | NA |

-continued

| Antibody/Probe | Commercial Source | Part # | Clone |
|---|---|---|---|
| HER2 (human epidermal growth factor receptor 2) mRNA 2X | Biosearch | NA | 2 |
| MTDH (metadherin) mRNA 2X | Biosearch | NA | 3 |

In addition to the above, the following non-limiting list of reagents and equipment were also utilized in Example 1: 1×PBS+2% BSA; 1×PBS+2% FBS/FCS; Microfuge tubes; Disposable 12×75 mm conical tubes (polypropylene); Pipetman or equivalent pipettors (2-20 µL, 20-200 µL, 200-1000 µL range): Vortex mixer; Centrifuge; Vacuum aspirator; 43° C.±1° C. waterbath.

Sample Preparation

Liquid samples were mixed by either vortexing gently at a medium setting for 1-2 seconds, or mixed by flicking the tube with a finger. Cells were observed to ensure cell pellet has been dissociated. Over-vortexing or rough handling of the cells will leads to excessive debris and affects results.

Tissue Aspiration and Fixation

Fine needle aspirate (FNA) samples were collected using the French Technique. Briefly, the French Technique involves an open-ended needle, without attached negative suction. Short, rapid strokes within the lesion cause dislodgement of cells and allow effective collection within the needle via capillary action. A syringe with the plunger removed may be attached for the collection of excess fluid. Regardless of the attachment used, the end of the apparatus must be open to the atmosphere to allow proper collection of the specimen; this opening must not be covered with a fingertip during the procedure, particularly when using a needle alone.

Breast tumor masses were aspirated according to this sampling technique. The breast tumor was sampled once and then, upon retrieval of the sample, the aspirate was injected directly into a vial containing 1 mL IncellFP.

mRNA Hybridization

Cells were fixed in 2 mL Reagent 1 upon arrival at IncellDx. A cell count was performed on the Cellometer to determine cell density and the volume to pipette for 400,000 cells, 400,000 cells were aliquoted to 3 12×75 mm tubes. Cells were washed in 1 mL Reagent 2 (pre-hybridization buffer 1), hand-mixed gently, and centrifuged at 600×g for 5 minutes at room temperature. Supernatant was aspirated, making sure the cell pellet was not disrupted; aspiration was performed on the opposite side of the tube. 1 mL Reagent 3 (pre-hybridization buffer 2) was added, cells were hand-mixed gently, and centrifuged at 600×g for 5 minutes at room temperature. Supernatant was aspirated as previously.

Hybridization cocktail was prepared by mixing the appropriate volumes of Reagent 4 (hybridization buffer) (101.5 µL per sample) and 1.5 µL of HER2 mRNA probe to tube 1 and 1.5 µL of MTDH mRNA probe to tube 2. 103 µL was added to each sample tube. Cells were hand-mixed gently. The reaction was allowed to incubate in preheated 43°±1° C. water bath for 30 minutes.

Cell Stringency Washes 1 mL pre-warmed Reagent 6 (stringency wash buffer 1) was added to each sample tube and the cells were hand-mixed gently. The cells were centrifuged at 600×g for 5 minutes at room temperature. The supernatant was aspirated as above. 1 mL pre-warmed Reagent 7 (stringency wash buffer 2) was added to each sample tube and the cells were hand-mixed gently. The reaction was allowed to incubate in 43° C. waterbath for 15 minutes. The cells were centrifuged at 600×g for 5 minutes at room temperature. The supernatant was aspirated as above.

Primary Antibody Hybridization Tubes 1&2

1 mL 1×PBS+2% BSA was added. The cells were centrifuged at 600×g for 5 min at room temperature. The supernatant was aspirated as above. 100 µL working dilutions of E-cadherin, ER, and PR primary antibodies were prepared as follows:

Tube 1: 5 µL of ER, and 5 µL of PR in 90 µL PBS+2% BSA.

Tube 2: 1 µL of E-cadherin in 99 µL of PBS+2% BSA.

The 100 µL E-cadherin antibody dilution was added to tube 2 and the 100 µL ER & PR antibody dilution was added to tube 1. The tubes were allowed to incubate at room temperature in the dark for 30 minutes. The cells were washed with 1 mL 1×PBS+2% FBS. The tubes were left to sit for 5 minutes at room temperature. The tubes were centrifuged at 400×g for 5 minutes at room temperature. The supernatant was aspirated as above. The wash, centrifuge and aspirate steps were repeated once.

Secondary Antibody Hybridization

100 µL working dilutions of the following were prepared:

Tube 1: 5 µL HER2 PE, 5 µL CD45, 1 µL Anti-rabbit 647, 89 PBS+2% BSA

Tube 2: 5 µL CD44, 5 µL CD45, 1 µL Anti-rabbit 647, 89 µL PBS+2% BSA

Tube 3: 2 µL Cleaved Caspase 3, 2 µL H2A.X, 2 µL Vimentin, 5 µL CD45, 89 µL PBS+2% BSA The 100 µL antibody dilutions were added to the appropriate tubes. The tubes were incubated at room temperature in the dark for 30 minutes. The cells were washed with 1 mL 1×PBS+2% FBS. The tubes were left to sit for 5 minutes at room temperature. The tubes were centrifuge at 400×g for 5 minutes at room temperature. The supernatant was aspirated as above. The wash, centrifuge and aspirate steps were repeated once.

DAPI Hybridization

A dilution of DAPI DNA dye in 1×PBS was prepared according to the following chart for a 5 mL aliquot:

| Desired concentration | DAPI Volume | PBS Volume |
|---|---|---|
| 1 µg/mL | 5 µL | 4995 µL |

200 µL of diluted DAPI was added to each sample tube and the cells were hand mixed gently. The cells were incubated at room temperature in the dark for 30 minutes after which the samples were ready for cytometric analysis on a flow cytometer equipped with 3 a three laser system.

Sample Analysis

Samples were collected on a EC800 flow cytometer (Sony Biotechnology Inc., San Jose, Calif.) under the Initial Breast Collection Protocol stopping on 30,000 total events.

Starting with Tube 1 (ER/PR/Her2/HER2/DAPI/CD45), a single cell gate Q was established and SSC/CD45 was applied. Gain was adjusted until the WBC region was in channel 200 as depicted in FIG. 1 and, once established, a compensation matrix was created by first applying FL1 comp into all other parameters, and continuing across with FL2, FL3, FL4 and FL5. The completed compensation matrix resembled FIG. 2.

Figures 2, 3:
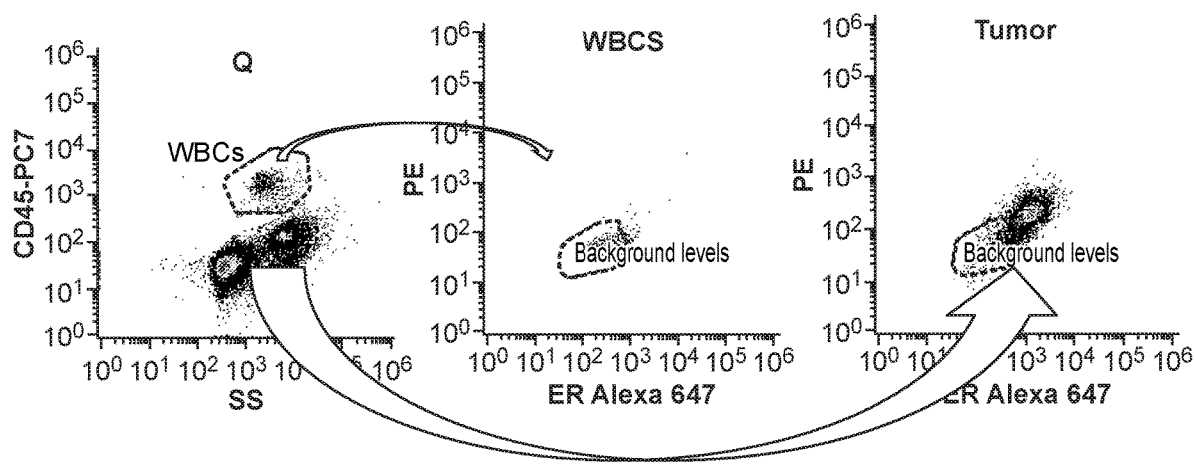
FIG. 2 depicts the compensation matrix generated for cells gated according to FIG. 1.
FIG. 3 depicts an example of the gated target cell populations for which data was generated.

Once the compensation was complete gating was applied to generate statistics on the target cell populations (FIG. 3). When gated the tumor population was outside the background levels when ER+ and this was the population for which ER mean fluorescence intensity (MFI), Her2 MFI and HER2 mRNA MFI was recorded. The % CD45+ was taken as the EIL (epithelial infiltrating leukocytes) as a mean of the three tubes. If the file had 30,000 events an FCS file was exported to be analyzed in ModFitLT for DNA index (DI) and % S-phase. Cell cycle region percentages were recorded.

Figure 4:
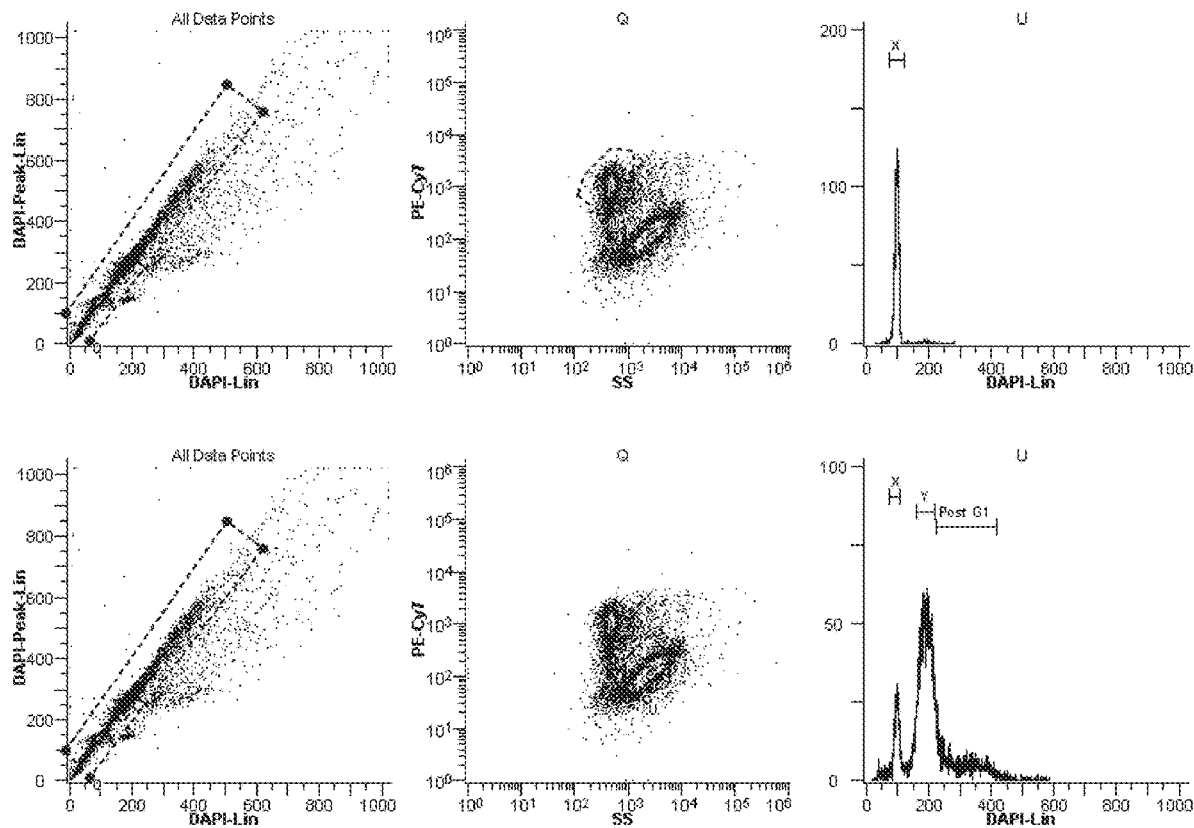
FIG. 4 depicts the generation of DNA index (DI) and cell cycle data.

In instances where 30,000 events were not generated, the MFI of Y (tumor) was divided by the MFI of the WBCs (X) to calculate the tumor DI (see FIG. 4). The % Post G1 was recorded as the mean of the three tubes. Data from the Clinical Performance Study comparing this manual technique to ModFitLT revealed a 100% concordance in DI and the post G1 was consistently higher than S-phase as predicted.

Continuing with Tube 2 (E-cadherin/CD44/MTDH mRNA/CD45/DAPI), again the WBCs were used to set the background level and the analysis approach for Tube 1 was repeated with Tube 2.

Figure 5:
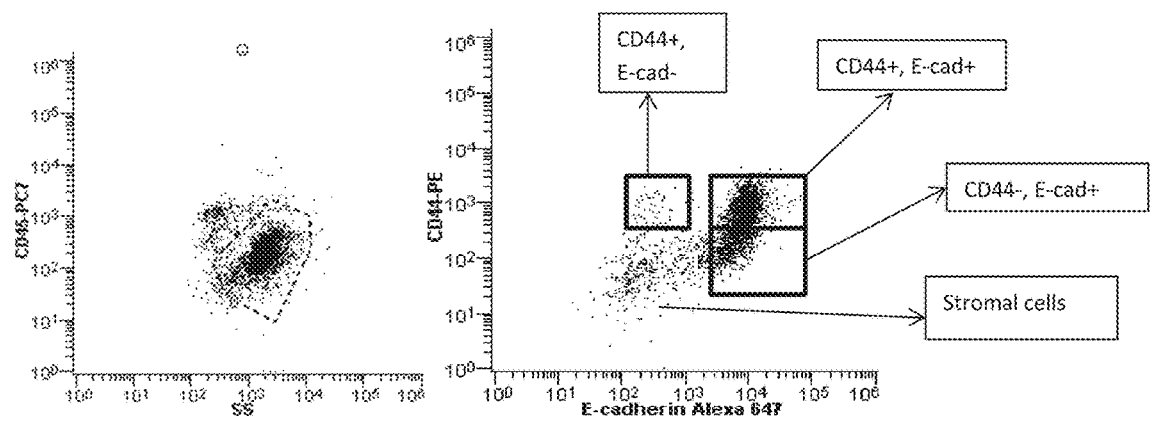
FIG. 5 depicts CD44 and E-cadherin expressing cell populations relevant to the metastasis model.

The MFI and % positive from the tumor population was recorded. The WBC's were used to determine where CD44 is positive (WBC's are >90%) (see FIG. 5). The ability to delineate these separate populations revealed statistical trends in the metastasis modeling.

The total readout of both tubes was added to the Phase II Breast database in which the metadata was meshed with the Cellular Multiplex data linked by Sample ID.

Overall Assay Specifications

To ensure longitudinal performance, each 3 months of the study breast cell sample results obtained were compared to an FNA mimic containing WBCs, MCF-7 and SK-BR-3 stained with all antibodies, mRNA probes and DAPI.

Figure 6:
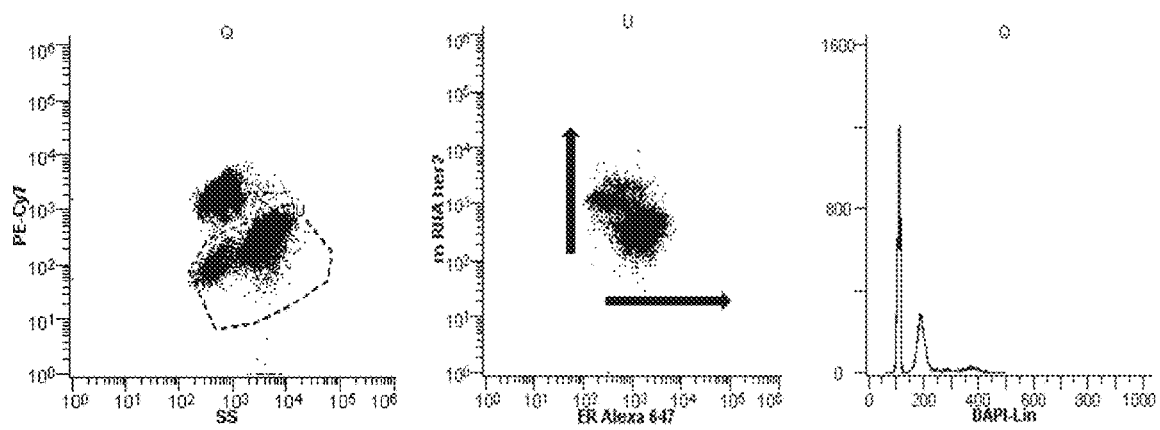
FIG. 6 depicts the her2 mRNA and estrogen receptor maker separation and resolvable WBC and tumor DNA indices of sample cell populations.

Samples were assayed for the following specifications: that the ER signal and the Her 2 mRNA signal separate in opposite directions, that the CD44 signal and MTDH mRNA separate in opposite directions, that the WBC and tumor mix DNA index are clearly resolvable (see FIG. 6).

Statistical Analysis

The Cellular Multiplex™ creates a series of variables (cytometric readouts as described above) which we link with metadata in an Excel spreadsheet. The raw .cdf files (cytometry data files) were analyzed by 2 different scientists before data was entered into the spreadsheet. Once agreed upon and checked for errors, a .csv file was ported for additional analysis.

Data of the breast cancer project was analyzed in R (R Core Team (2014) *R: A Language and Environment for Statistical Computing*, Vienna, Austria; www(dot)R-project (dot)org). First, the minimum, first quartile, median, mean, third quartile and maximum of each variables for both healthy and unhealthy groups were calculated and box plots for comparing the two groups were created. Second, nonparametric Mann-Whitney-Wilcoxon analysis was used to decide whether the population distributions of each variable for both healthy and unhealthy groups were identical without assuming them to follow a normal distribution. Once difference was established, Tree-Based Models and Random forests were used to create a classification and regression. Finally, a linear regression model was applied to our data to separate healthy groups form unhealthy groups.

The entire two tube set creates 19 total variables on each case; this large number reduces the overall sample size to 32 tumors and 6 normal cases. The full model contains the following variables: Total.Cell.Count, Count.single.cells, Count.epithelial.cells, Mean.G1 . . . Epithelial, X . . . Gated . . . G1., X . . . CD45.EIL, X.ER.PR . . . WBCS, X.Her2.mRNA . . . Epithelial, X.HER2.protein . . . Epithelial, X . . . CD44.Epithelial, X . . . E.cadherin . . . CD44 . . . Epithelial, MCV.Epithelial, Cellometer.Count and iCyt.Count. The coefficients for the variables are provided below:

| Variable | Coefficient |
| --- | --- |
| (Intercept) | 1.677413e+01 |
| Total.Cell.Count | 1.674432e−06 |
| Count.single.cells | 1.015261e−04 |
| Count.epithelial.cells | 1.122740e−04 |
| Mean.G1..Epithelial | 1.890142e−02 |
| X..Gated..G1 | 1.499511e−01 |
| X..CD45.EIL | 2.030679e−02 |
| X.ER.PR..WBCS | −4.266666e−03 |
| X.Her2.mRNA..Epithelial | −1.296829e−05 |
| X.HER2.protein..Epithelial | 1.088247e−03 |
| X..CD44.Epithelial | 2.834147e−02 |
| E.cadherin..CD44...Epithelial | −3.149327e−03 |
| MCV.Epithelial | 1.650797e−03 |
| Cellometer.Count | 3.486292e−07 |
| iCyt.Count | 2.258215e−06 |

The variable number was then reduced based on the p values of the derived results followed with a forward and back step method to find a reduced model. As a result, the final model contained 5 variables: Mean.G1 . . . Epithelial, X . . . Gated . . . G1., X.ER.PR . . . WBCS, MCV.Epithelial and iCyt.Count. The final coefficients for the reduced model are provided below:

| Variable | Coefficient |
| --- | --- |
| (Intercept) | 2.430566e+01 |
| Mean.G1..Epithelial | −3.129160e−02 |
| X..Gated..G1 | −1.889957e−01 |
| X.ER.PR..WBCS | −5.304748e−03 |
| MCV.Epithelial | 1.745426e−03 |
| iCyt.Count | 2.473201e−06 |

Figure 7:
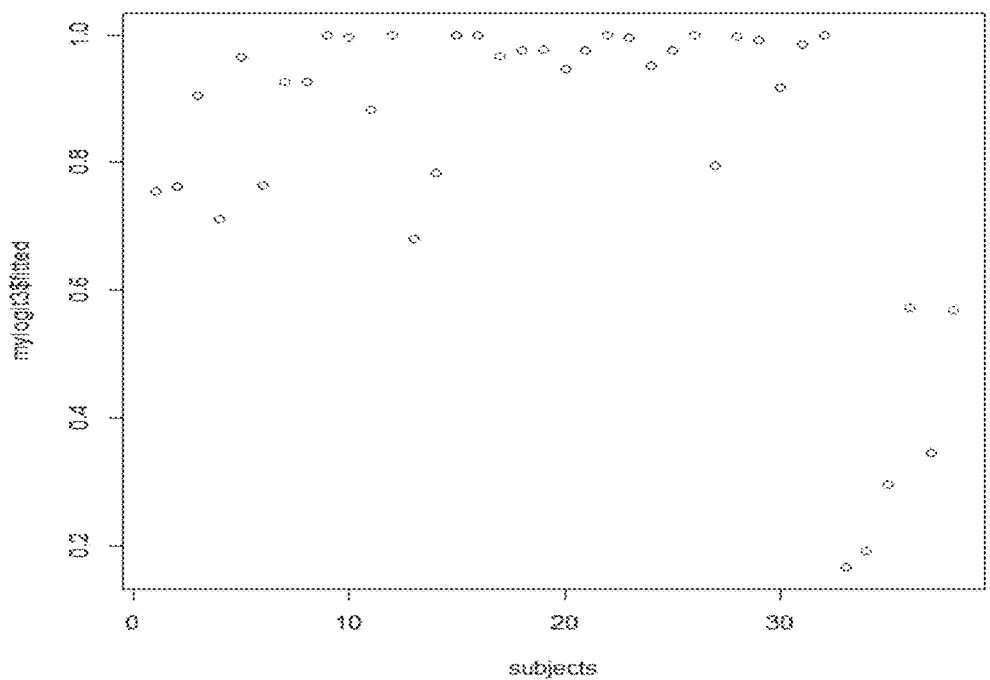
FIG. 7 depicts the statistical separation of samples from tumor and healthy subjects using the 5 variable reduced model.

A visual representation of this statistical analysis as it pertains to the subjects from which the samples were derived is provided in FIG. 7. Statistically, the 5 variables listed above separate a "tumor" cell from a "healthy" cell in that they are not identical.

Regarding what these variables measure and how they relate to cancer is discussed below. The Mean G1 Epithelial compares the DNA content of tumor epithelial to the DNA content of healthy cells (see FIG. 4 for a relevant graphical description). This reflects a difference in genomic integrity and may indicate, without being bound to theory, the insertion/deletion of DNA strips into the cancerous cells. The Gated G1 refers to the % of cells in G1 of the cell cycle. From the statistical analysis it is clear that the resting and proliferative components of the cell cycle differ when comparing tumor versus normal. The ER/PR WBCs represents the background levels of the markers on the white cell infiltrate. This statistical difference was an unexpected statistical finding. The MCV Epithelial refers to the Mean Corpuscular Volume (Coulter Volume) of the individual cells. This statistical difference represents a digital signature of the difference in morphology of a tumor cell versus a normal cell. In a series of experiments prior to beginning this study, a "true" size difference of cancer cells (SK-BR-3 and MCF-7) versus Normal Human Mammary Cells (HMEC) was confirmed in the unfixed and fixed state. In these same studies, it was confirmed that cells fixed in IncellFP™ maintained 90% of the unfixed MCV. The last variable is iCyt count which is the number of cells passing thru the flow cell in 300 ul of fluid. This statistical difference represents that the FNA of the tumor space contains more cells than a normal duct contains.

Figure 8:
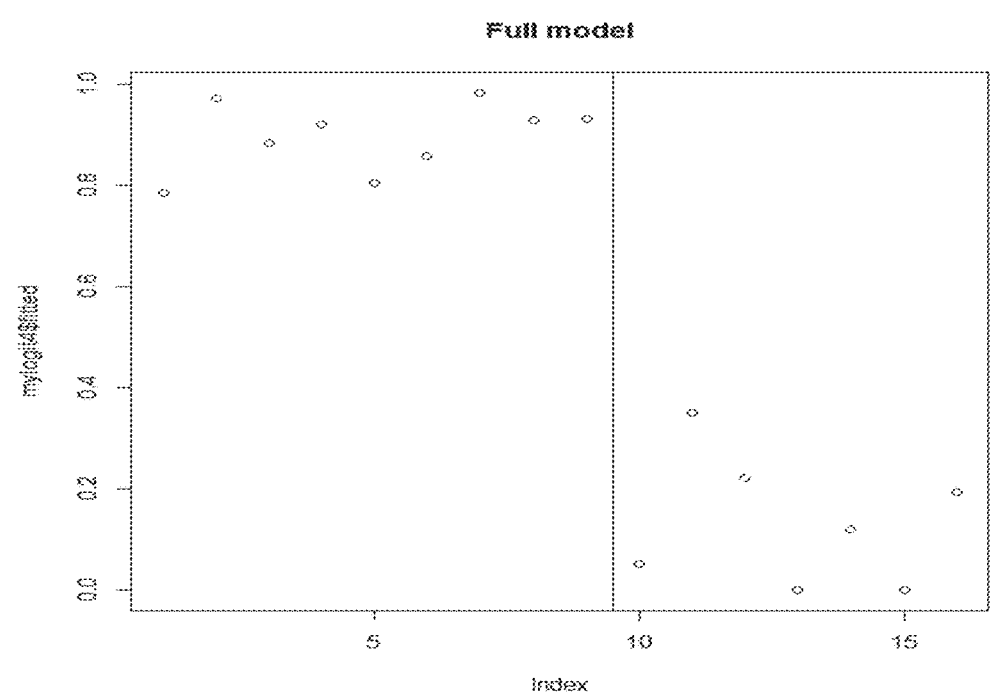
FIG. 8 depicts statistical separation of samples from metastatic tumors and non-metastatic tumors using the full metastasis model.

The metastatic model followed the same process as above with fewer cases due to the inclusion of MTDH, which was added at the midpoint of the study, and the clear definition of metastasis in the metadata. The full model contains the following 18 variables: Total.Cell.Count, Count.single.cells, Count.epithelial.cells, Mean.G1 . . . Epithelial., Mean.G1.WBC, X . . . CD45.EIL, X . . . E.Cadherin.Epithelial, X.ER.PR . . . Epithelial, X.ER.PR . . . WBCS, X.Her2.mRNA . . . Epithelial, X.HER2.protein . . . Epithelial, X.MTDH.mRNA . . . Epithelial, X . . . CD44.Epithelial, X . . . E.cadherin . . . CD44 . . . Epithelial, MCV.Epithelial.iCyt.Count and Cellometer.Count. A visual representation of the statistical analysis based on the Full Model is provided in FIG. 8. The coefficients for the variables are provided below:

| Variable | Coefficient |
| --- | --- |
| (Intercept) | 2.208197e+00 |
| Total.Cell.Count | 1.810922e−06 |
| Count.single.cells | 3.640926e−05 |
| Count.epithelial.cells | 5.714827e−05 |
| Mean.G1..Epithelial | 5.756775e−03 |
| Mean.G1.WBC | −1.809671e−04 |
| X..CD45.EIL | −4.675704e−02 |
| X..E.Cadherin.Epithelial | −8.957555e−04 |
| X.ER.PR..Epithelial | 9.315181e−05 |
| X.ER.PR..WBCS | −2.078572e−03 |
| X.Her2.mRNA..Epithelial | 9.457119e−04 |
| X.HER2.protein..Epithelial | 1.547739e−03 |
| X.MTDH.mRNA..Epithelial | −3.113753e−04 |
| X..CD44.Epithelial | 2.866543e−02 |
| X...E.cadherin..CD44...Epithelial | 1.424379e−02 |
| MCV.Epithelial | −2.729672e−04 |
| iCyt.Count | 1.937675e−06 |
| Cellometer.Count | −3.300775e−06 |

Figure 9:
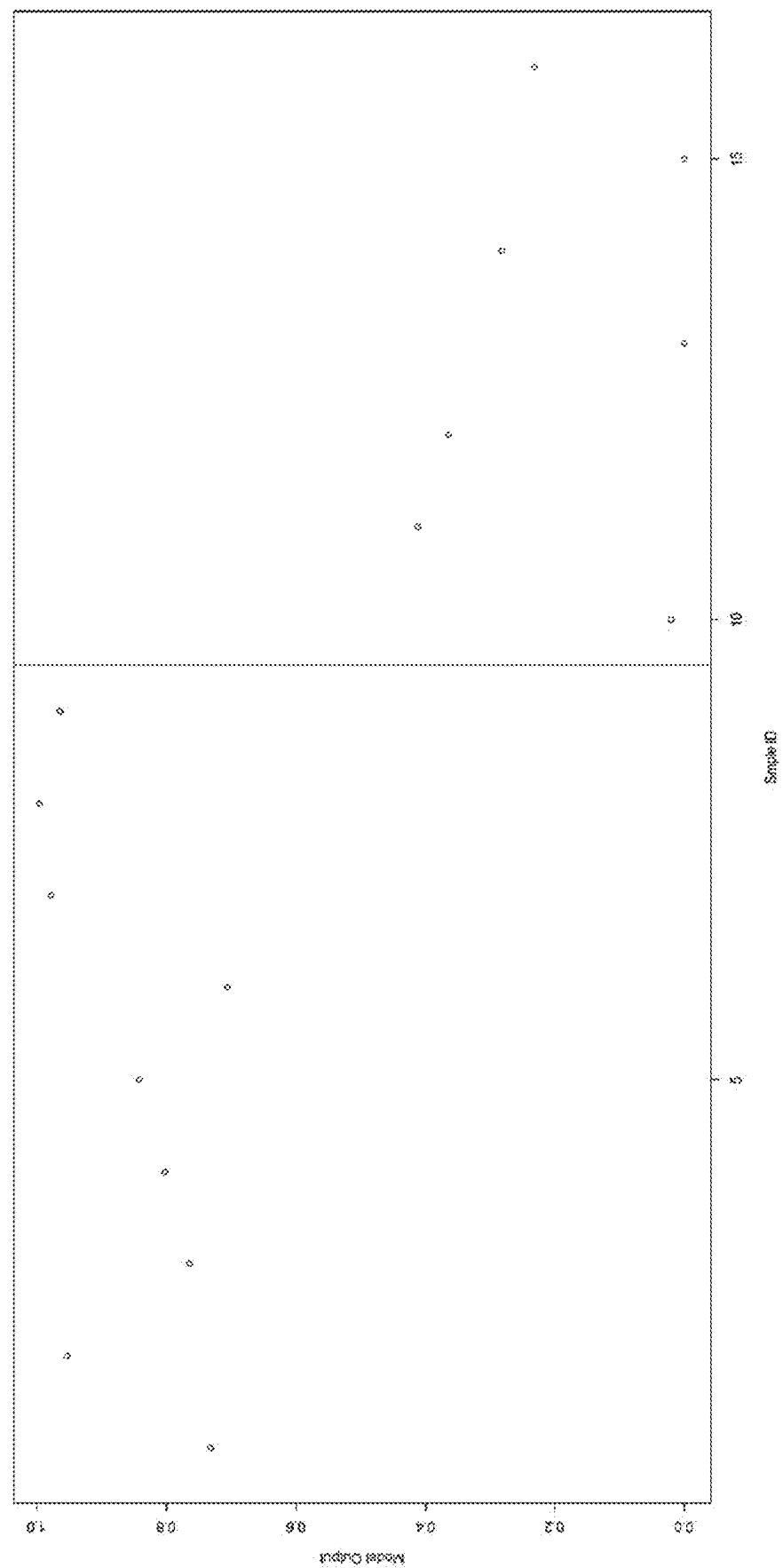
FIG. 9 depicts statistical separation of samples from metastatic tumors and non-metastatic tumors using the reduced metastasis model.

The variables were then minimized based on the p values of the results and forward and back step methods to find a reduced model, the final model has 6 variables: HER2.protein . . . Epithelial, Count.single.cells, Count.epithelial.cells, Mean.G1 . . . Epithelial, Mean.G1.WBC and Cellometer.Count. A visual representation of the statistical analysis based on the Reduced Model is provided in FIG. 9. The coefficients of the final model are provided below:

| Variable | Coefficient |
| --- | --- |
| Count.single.cells | 6.269065e−05 |
| Count.epithelial.cells | 1.320985e−04 |
| Mean.G1..Epithelial | 4.083481e−03 |
| Mean.G1.WBC | −6.268965e−03 |
| X.HER2.protein..Epithelial | 2.046613e−03 |
| Cellometer.Count | −3.962722e−06 |

Example 2

Samples and Data Collection

Data was collected by flow cytometry essentially as described above for a set of breast cancer samples (i.e., breast cancer tissue) and a set of healthy samples (i.e., normal breast tissue). Various parameters were obtained including those that were imported to build the classification model as described below.

Model Generation

Parameters measured from the breast cancer tissue and healthy breast tissue datasets were used to generate a classification model. The following parameters were used: Total Cell Count, Count Single Cells, Count Epithelial Cells, MCV Epithelial, Mean G1 WBC, Mean G1 Epithelial, Percent G1 Epithelial, DNA Index(s), Percent Post G1 Epithelial, Percent CD45 EIL, (ER/PR) WBCs, Percent ER/PR Epithelial, (ER/PR) Epithelial, (Her2 mRNA) Epithelial, (HER2 protein) Epithelial, MTDH mRNA, Percent CD44+E-cadherin+Epithelial, Percent E-Cadherin+CD44−Epithelial, (Percent E-cadherin-CD44+) Epithelial, Percent Vimentin Epithelial, Percent Caspase 3 Epithelial, and Percent p H2A.X Epithelial.

Figure 12:
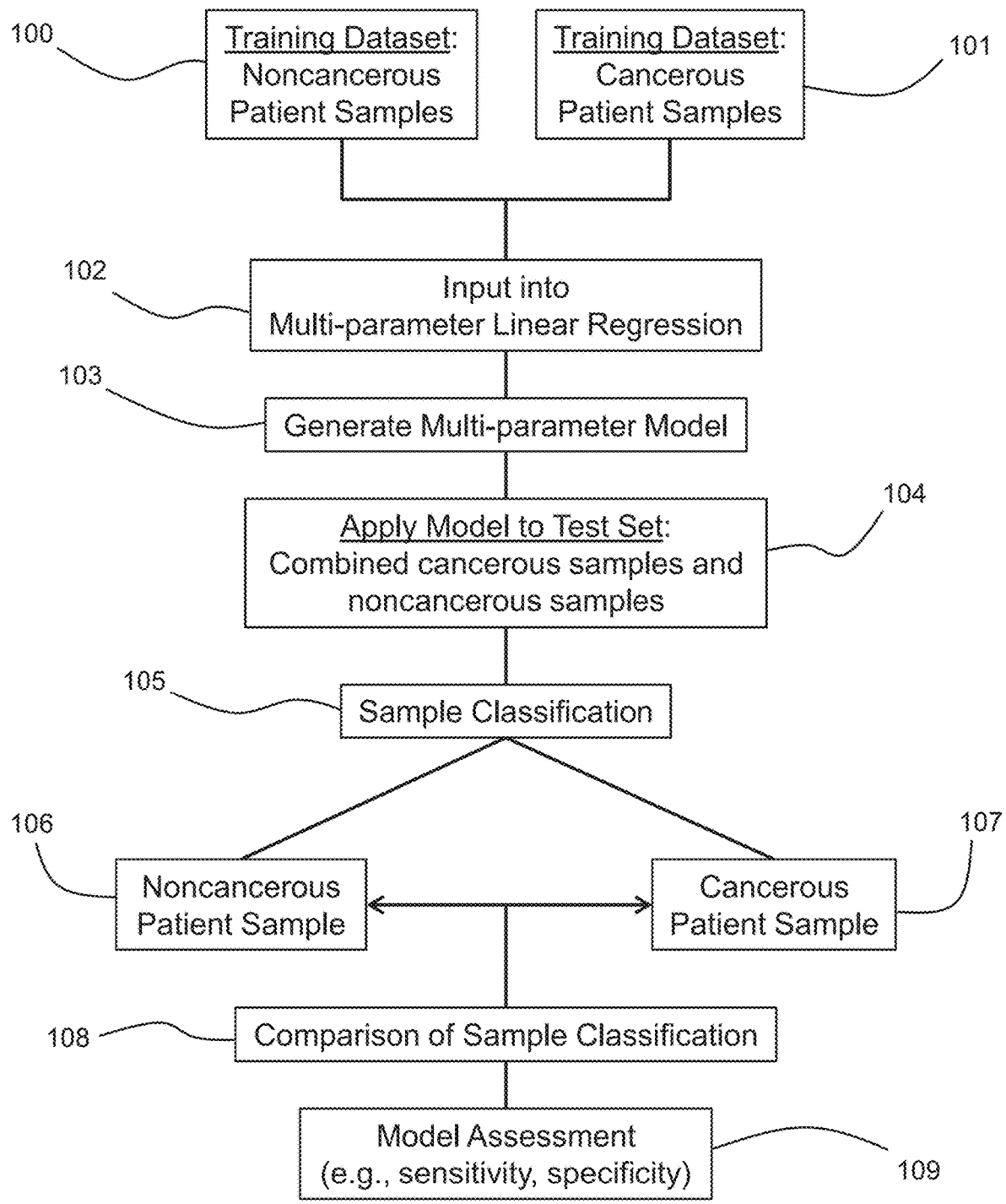
FIG. 12 provides a flow chart showing a process for generation and assessment of a multi-parameter model for cancer and non-cancer sample classification.

The general scheme for generating and assessing a multi-parameter model is provided in the flow chart presented in FIG. 12. Briefly, the training datasets for non-cancerous (100) and cancerous (101) samples were imported into a general linear regression model (102). In this example, the data for the above parameters was imported into the following general linear regression model:

$$Y = \begin{cases} 1 & \text{cancer} \\ 0 & \text{non-caner} \end{cases}$$

$$\pi(x) = P(Y=1) = \frac{\exp(\alpha + \beta_1 * x_1 + \beta_1 * x_1 + \beta_2 * x_2 + \beta_3 * x_3 + \beta_4 * x_4 + \beta_5 * x_5)}{1 + \exp(\alpha + \beta_1 * x_1 + \beta_1 * x_1 + \beta_2 * x_2 + \beta_3 * x_3 + \beta_4 * x_4 + \beta_5 * x_5)}$$

Figure 10:
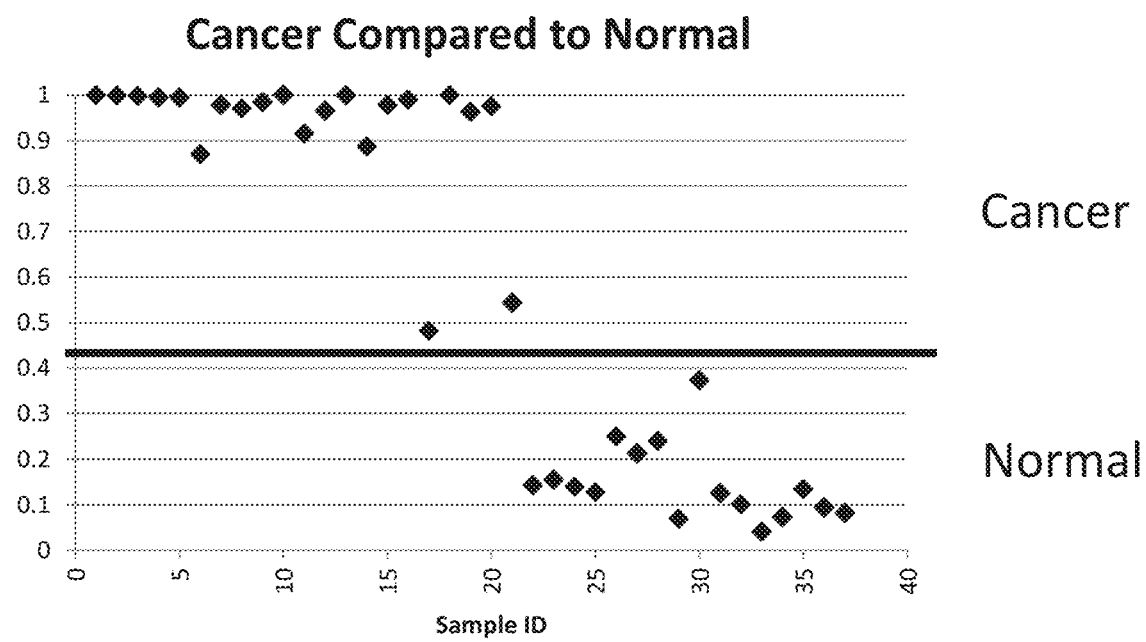
FIG. 10 depicts cancer vs. normal sample classification according to a multi-parameter model as described herein.
Figure 11:
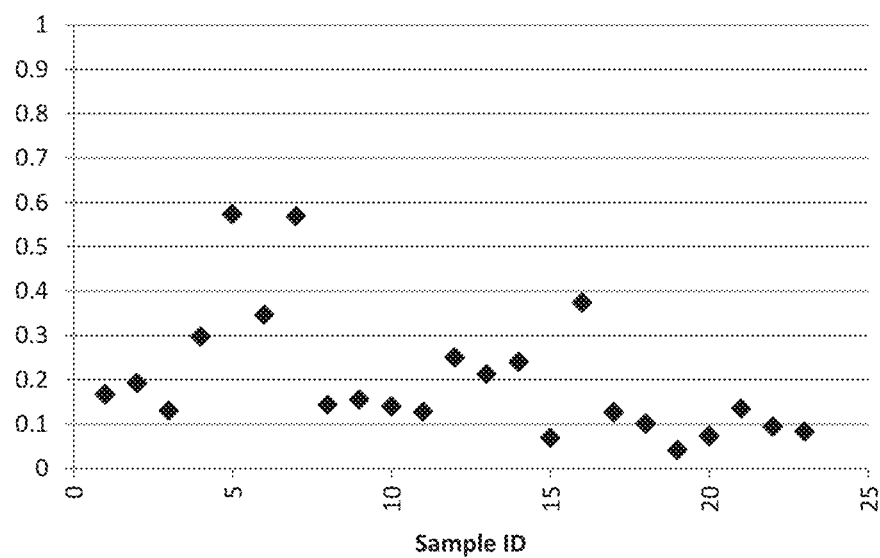
FIG. 11 depicts control comparisons of normal samples relevant to FIG. 10.

The linear regression generated a multi-parameter model (103) containing a defined set of parameters (i.e., a multi-parameter model). The model was applied to a test set of samples that contained both healthy (noncancerous) and cancerous samples (104). The multi-parameter model was used to for sample classification of the test set (105) to identify samples as either noncancerous (106) or cancerous (107). The sample classification based on the multi-parameter model was compared (108) and the comparison was used for classification assessment (109) to determine the sensitivity and specificity of the generated multi-parameter model. The example provided, the model produced a classification model that classified cancer versus non-cancer samples with 95% sensitivity and 95% specificity. A graphical representation of sample classification of breast cancer and normal breast tissue samples using this model is presented in FIG. 10. As a control, comparisons using the model were also performed between normal samples, e.g., as depicted in FIG. 11.

This example demonstrates the ability to build a classification multi-parameter model from the individual measured parameters listed above. These results demonstrate that such a model can be used to successfully classify breast cancer and normal tissue samples with high specificity and sensitivity.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method of assessing a cellular breast sample, the method comprising:
   a) flow cytometrically analyzing the cellular breast sample to obtain:
      i) sample data comprising sample cell density data;
      ii) epithelial cell data comprising DNA content data, proliferation data and cell volume data; and
      iii) white blood cell (WBC) data comprising one or both of breast cancer biomarker data and sample percentage of WBC data; and
   b) evaluating the flow cytometrically obtained:
      sample data by comparing the sample cell density data to a reference value,
      epithelial cell data by comparing one or more of the DNA content data, proliferation data and, cell volume data to reference values, and
      WBC data by comparing one or both of the breast cancer biomarker data and the sample percentage of WBC data to reference values,
to assess the cellular breast sample.

2. The method according to claim 1, wherein the WBC data comprises breast cancer biomarker data comprising the level of at least one breast cancer biomarker in a population of WBCs.

3. The method according to claim 2, wherein the at least one breast cancer biomarker comprises estrogen receptor, progesterone receptor, or a combination thereof.

4. The method according to claim 1, wherein the cellular breast sample is a fine needle aspirate sample.

5. The method according to claim 1, wherein the method further comprises fixing and permeabilizing the cells of the cellular breast sample.

6. The method according to claim 1, wherein the method further comprises contacting the cells of the cellular breast sample with a label under conditions sufficient to produce a labeled cellular breast sample.

7. The method according to claim 1, wherein the method further comprises contacting the cells with one or more wash solutions.

8. The method according to claim 1, wherein the cellular breast sample is obtained from a subject and the evaluating comprises assessing whether the subject has a neoplastic disease.

9. The method according to claim 8, wherein the neoplastic disease is breast cancer.

10. The method according to claim 1, wherein the reference value to which the sample cell density data is compared is 50,000 or more cells per volume of analyzed sample,
   the reference value to which the DNA content data is compared is greater than or equal to 1.05 times the DNA content of a control,
   the reference value to which the proliferation data is compared is at least 20% more than the proliferation of a control,
   the reference value to which the cell volume data is compared is greater than or equal to 1.50 times the cell volume of a control,
   the reference value to which the breast cancer biomarker data is compared is a level of the biomarker less than or equal to 0.95 times a level of the breast cancer biomarker present in WBCs of a control, or
   a combination thereof.

* * * * *

UNITED STATES PATENT AND TRADEMARK OFFICE
CERTIFICATE OF CORRECTION

PATENT NO. : 10,627,389 B2
APPLICATION NO. : 15/164778
DATED : April 21, 2020
INVENTOR(S) : Keith Shults et al.

It is certified that error appears in the above-identified patent and that said Letters Patent is hereby corrected as shown below:

In the Specification

Column 33, Lines 7-8, replace "e.g., 2 or more, 3 or more, 4 or more, 5 or more, or more, etc." with -- e.g., 2 or more, 3 or more, 4 or more, 5 or more, 10 or more, etc. --

Signed and Sealed this
Twenty-sixth Day of May, 2020

Andrei Iancu
*Director of the United States Patent and Trademark Office*